US007067550B2

(12) United States Patent
Ingram et al.

(10) Patent No.: US 7,067,550 B2
(45) Date of Patent: Jun. 27, 2006

(54) TREATMENTS FOR NEUROTOXICITY IN ALZHEIMER'S DISEASE

(75) Inventors: Vernon M. Ingram, Cambridge, MA (US); Barbara J. Blanchard, Cambridge, MA (US); Brent R. Stockwell, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/143,534

(22) Filed: May 10, 2002

(65) Prior Publication Data

US 2003/0105152 A1 Jun. 5, 2003

Related U.S. Application Data

(63) Continuation-in-part of application No. 10/051,663, filed on Jan. 18, 2002, which is a continuation-in-part of application No. 09/706,574, filed on Nov. 3, 2000.

(51) Int. Cl.
A61K 31/4035 (2006.01)
(52) U.S. Cl. .................................................. 514/417
(58) Field of Classification Search .................... 435/6; 514/2, 445, 523, 525, 417
See application file for complete search history.

(56) References Cited

U.S. PATENT DOCUMENTS

| | | | |
|---|---|---|---|
| 4,801,575 A | 1/1989 | Pardridge | |
| 4,902,505 A | 2/1990 | Pardridge et al. | |
| 4,918,162 A | 4/1990 | Slamon et al. | |
| 4,933,324 A | 6/1990 | Shashoua | |
| 4,975,430 A | 12/1990 | Jahr et al. | |
| 5,004,697 A | 4/1991 | Pardridge | |
| 5,108,921 A | 4/1992 | Low et al. | |
| 5,112,596 A | 5/1992 | Malfroy-Camine | |
| 5,268,164 A | 12/1993 | Kozarich et al. | |
| 5,385,915 A * | 1/1995 | Buxbaum et al. | 514/313 |
| 5,391,723 A | 2/1995 | Priest | |
| 5,434,050 A | 7/1995 | Maggio et al. | |
| 5,442,043 A | 8/1995 | Fukuta et al. | |
| 5,491,144 A | 2/1996 | Trinks et al. | |
| 5,506,206 A | 4/1996 | Kozarich et al. | |
| 5,525,727 A | 6/1996 | Bodor | |
| 5,527,527 A | 6/1996 | Friden | |
| 5,552,415 A | 9/1996 | May | |
| 5,552,426 A | 9/1996 | Lunn et al. | |
| 5,576,209 A | 11/1996 | Bredesen | |
| 5,639,726 A | 6/1997 | Lawrence et al. | |
| 5,663,336 A | 9/1997 | Trinks et al. | |
| 5,703,129 A * | 12/1997 | Felsenstein et al. | 514/613 |
| 5,817,626 A | 10/1998 | Findeis et al. | |
| 5,948,763 A | 9/1999 | Soto-Jara et al. | |
| 6,172,043 B1 | 1/2001 | Ingram et al. | |
| 6,552,066 B1 * | 4/2003 | Sharpe et al. | 514/419 |
| 2003/0105152 A1 * | 6/2003 | Ingram et al. | 514/417 |
| 2003/0114510 A1 | 6/2003 | Ingram et al. | |

FOREIGN PATENT DOCUMENTS

| | | |
|---|---|---|
| WO | WO 96/37212 A1 | 11/1996 |
| WO | PCT/US96/10220 A1 | 12/1996 |
| WO | WO 98/08868 A1 | 3/1998 |
| WO | WO 98/30229 A1 | 7/1998 |

OTHER PUBLICATIONS

Anwer et al., *Int. J. Pep. Protein Res.* 36:392-399, 1990.
Arispe et al., *Proc. Nat'l Acad. Sci. USA* 90:10573-10577, 1993.
Arispe et al., *Proc. Nat'l Acad. Sci. USA* 90:567-571, 1993.
Blanchard et al., *Brain Res* 776(1-2):40-50, 1997.
Lam, *Nature* 354:82-84, 1991.
Levine, *Protein Sci* 2:404-410, 1993.
Mattson et al., *J. Neurosci.* 12:376-389, 1992.
Nachman et al., *Regul. Pept.* 57:359-370, 1995.
Rivera-Baeza et al., *Neuropeptides* 30:327-333, 1996.
Shen et al., *Biophys J.* 65:2383-2395, 1993.
Soto et al., *Biochem. Biophys. Res. Commun.* 226:672-680, 1996.
Spatola et al, *Chemistry & Biochemistry of AA, Peptides & Proteins (Weinstein, Ed.)* vol. 7, pp. 267-356, 1983.*
Tomski and Murphy, *Arch. Biochem. Biophys.* 294:630-638, 1992.
Blanchard et al., *J. Alzheimer's Disease* 2(2):137-149 (2000).
Bräuner et al., *Biochim Biophys Acta* Apr. 11, 1984;771(2):208-16.
Cooper et al., *Biochemistry.* 29:3859-3865 (1990).
Durell et al., *Biophys. J.* 67:2137-2145 (1994).
Hartinger, *J. Biol. Chem.* 268:23122-23127 (1993).
Hartley et al., *J. Neuroscience* 19:8876-8884 (1999).
Kawahara et al., *Biophys. J.* 73:67-75 (1997).
Langheinrich, et al., *J. Physiol.* 502 ( Pt 2):397-408 (1997).
Pollard et al., *Ann. N.Y. Acad. Sci.* 695:165-168 (1993).

(Continued)

Primary Examiner—Bennett Celsa
(74) Attorney, Agent, or Firm—Wolf, Greenfield and Sacks, P.C.

(57) ABSTRACT

The invention involves identification of a mechanism of β-amyloid peptide cytotoxicity, which enables treatment of conditions caused by β-amyloid peptide aggregates by administration of compounds which antagonize the mechanism of cytotoxicity. The invention includes the identification and isolation of compounds which can reduce the neurotoxic effects of such aggregates. Methods for treating conditions resulting from neurotoxic β-amyloid peptide aggregates, such as Alzheimer's disease and pharmaceutical preparations are provided. Also provided are methods for selecting additional compounds which can reduce the neurotoxic effects of β-amyloid aggregates.

2 Claims, 11 Drawing Sheets

OTHER PUBLICATIONS

Sanderson et al., *Brain Res.* 744:7-14 (1997).
Walsh et al., *J. Biol. Chem.* 274:25945-52 (1999).
Yankner et al., *Science.* 250:279-282 (1990).
O'Dell, T. J. et al., Nature vol. 353 (6344), (Sep. 1991) pp. 558-560.
Franco, R., et al., Eur. J. Physiol. vol. 442 (Jun. 2001) pp. 791-800.
Dieter, M.Z., et al., Biochemical Pharmacology, vol. 61(2) (Jan. 2001) pp. 215-225.
Tjernberg et al., Arrest of beta-amyloid fibril formation by a pentapeptide ligand. J Biol Chem. Apr. 12, 1996;271(15):8545-8.
Tjernberg et al., Controlling amyloid beta-peptide fibril formation with protease-stable ligands. J Biol Chem. May 9, 1997;272(19):12601-5.

* cited by examiner

Fig. 1 Aβ1-42 -/+ CNQX

Fig. 2  TRIS blocking

Fig. 4  TTX

Fig. 5   Tyr/0Ca

SEQUENCE LISTING

```
<160> NUMBER OF SEQ ID NOS: 3

<210> SEQ ID NO 1
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 1

Gly Ser Asn Lys Gly Ala Ile Ile Gly Leu Met
1               5                   10

<210> SEQ ID NO 2
<211> LENGTH: 42
<212> TYPE: PRT
<213> ORGANISM: Artificial Sequence
<220> FEATURE:
<223> OTHER INFORMATION: Synthetic Peptide

<400> SEQUENCE: 2

Asp Ala Glu Phe Arg His Asp Ser Gly Tyr Glu Val His His Gln Lys Leu
1               5                   10                  15

Val Phe Phe Ala Glu Asp Val Gly Ser Asn Lys Gly Ala Ile Ile Gly Leu
            20                  25                  30

Met Val Gly Gly Val Val Ile Ala
35                  40

<210> SEQ ID NO 3
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 3
```

-continued

```
Asp Ala Glu Phe Arg His Asp Ser Gly Tyr Glu Val His His Gln Lys Leu
 1               5                  10                  15
Val Phe Phe Ala Glu Asp Val Gly Ser Asn Lys Gly Ala Ile Ile Gly Leu
            20                  25                  30
Met Val Gly Gly Val Val
 35              40
```

TREATMENTS FOR NEUROTOXICITY IN ALZHEIMER'S DISEASE

RELATED APPLICATIONS

This application is a continuation-in-part of U.S. application Ser. No. 10/051,663, filed Jan. 18, 2002, now pending, which is a continuation-in-part of U.S. application Ser. No. 09/706,574, filed Nov. 3, 2000, now pending.

FIELD OF THE INVENTION

The invention relates to compounds which antagonize the neurotoxic effects of β-amyloid peptide aggregates, methods for using such compounds and methods for discovering compounds which also antagonize the neurotoxic effects of β-amyloid peptide aggregates.

BACKGROUND OF THE INVENTION

The post-mortem pathology of Alzheimer's Disease is characterized by the presence in particular regions of the brain of many extracellular plaques and of many intracellular neurofibrillary tangles, whose density correlates with the severity of dementia. There is also massive, but regional, neuronal cell disfunction and cell loss, caused presumably by the reported neurotoxicity of the β-amyloid peptides (also referred to herein as βAP and Aβ) which are components of senile plaques. The cytotoxicity of the β-amyloid peptides was first established in primary cell cultures from rodent brains and also in human cell cultures. These were relatively long-term experiments, lasting for a few days. The immediate molecular cause of the cytotoxicity was not clear from these reports. The work of Mattson et al. (*J. Neurosci.* 12:376–389, 1992) indicates that β-amyloid peptides, including the sequence Aβ25–35, in the presence of the excitatory neurotransmitter glutamate causes an immediate increase in intracellular calcium, which, it is supposed, is very toxic to the cell through its greatly increased second messenger activities.

The formation of pathological β-amyloid peptides in Alzheimer's Disease is not well understood. The amyloid precursor protein (APP) is a very large transmembrane protein whose normal turnover degradation cleaves the presumptive β-amyloid peptide in the middle, thus making it inactive as a neurotoxic agent. In addition, the future C-terminus of β-amyloid peptides is buried in the middle of the lipid membrane. How the degradation of APP is altered in Alzheimer's Disease (AD) is only gradually becoming clear with no convincing explanation at present.

There are three β-amyloid peptides, $βAP_{1-42}$, $βAP_{1-40}$, and $βAP_{25-35}$ (also referred to herein as Aβ1–42, Aβ1–40 and Aβ25–35, respectively), which are homologous to the tachykinin neuropeptides. All three peptides are strongly neurotoxic when applied to cultured cells. Aβ1–40 and Aβ1–42 are the most prominent components of senile plaques. It is not clear whether $βAP_{25-35}$ occurs in the brains of AD individuals. $βAP_{25-35}$ might be absent because it has been scavenged when dead neurons are removed.

The $βAP_{1-42}$ peptide, and related shorter peptides, are cytotoxic towards cultured neuronal cells at micromolar concentrations, but neurotrophic at nanomolar concentrations. Others have observed that the peptide is cytotoxic also in vivo. Variability in results from different laboratories perhaps can be ascribed to the different propensities of particular β-amyloid peptides to aggregate in aqueous solution. It has been suggested that long-term cytotoxicity resides in insoluble aggregates. The molecular mechanism of this cytotoxicity is not well known, perhaps because most of the reported experiments examine chronic cytotoxic effects only after 24–48 hours of exposure to insoluble aggregates of β-amyloid peptides.

The ability of β-amyloid peptides such as Aβ1–40 to form cation-selective ionophores was postulated earlier as a mechanism for cytotoxicity (Arispe et al., *Proc. Nat'Acad. Sci. USA* 90:10573–10577, 1993; Arispe et al., *Proc. Nat'l Acad. Sci. USA* 90:567–571, 1993). However, these experiments were carried out in artificial membranes. While in actual cells the ionophore mechanism might indeed be an important factor, there are at least two other mechanisms: interaction between the β-amyloid peptides with existing ion channels, and penetration of the peptides into the cell with consequent release of calcium from internal stores.

Thus, while the precise mechanism of neurotoxicity of β-amyloid peptides in Alzheimer's Disease has not been definitively established, there is a need to determine which of the aforementioned mechanisms of cytotoxicity is the cause of neuronal cell death in AD. Identification of the cytotoxic mechanism is needed to enhance the prospects of designing compounds capable of antagonizing the effects of aggregation of β-amyloid peptides.

SUMMARY OF THE INVENTION

The invention involves in one aspect identification of a mechanism of β-amyloid peptide cytotoxicity, which enables treatment of conditions caused by β-amyloid peptide aggregates by administration of compounds which antagonize the mechanism of cytotoxicity. In a further aspect, the invention involves the identification and isolation of compounds that counteract or inhibit the effects of increased neuronal cell calcium influx induced by the presence of β-amyloid peptide (Aβ). The invention involves in another aspect the identification and isolation of antagonists of β-amyloid peptide induced neuronal depolarization by high throughput screening of libraries of compounds.

According to one aspect of the invention, methods for treating Alzheimer's disease are provided. The methods include contacting a neuronal cell with an amount of a composition comprising one or more compounds that decrease membrane depolarization of neuronal cells caused by aggregated β-amyloid (Aβ) protein degradation products, effective to decrease the membrane depolarization. In some embodiments, the membrane depolarization is decreased to about 80% of its value in the absence of the composition. Preferably, the membrane depolarization is decreased to about 75% of its value in the absence of the composition. More preferably, the membrane depolarization is decreased to about 70% of its value in the absence of the composition. Still more preferably, the membrane depolarization is decreased to about 65% of its value in the absence of the composition. Most preferably, the membrane depolarization is decreased to about 60% of its value in the absence of the composition.

Preferably the composition comprises one or more compounds selected from the group consisting of tyrosine kinase inhibitors, chloride channel antagonists, dopamine receptor agonists, alpha2-adrenergic receptor antagonists and $mGluR_1$ antagonists. In certain embodiments, the tyrosine kinase inhibitor inhibits EGF receptor tyrosine kinase. Preferably the tyrosine kinase inhibitor is selected from the group consisting of 4,5-dianilinophthalimide (DAPH1) and tyrphostin 47. In other embodiments, the tyrosine kinase inhibitor inhibits TrkA receptor tyrosine kinase. Preferably such a tyrosine kinase inhibitor is tyrphostin AG879. In still other embodiments, the chloride channel antagonist is selected from the group consisting of nafoxidine and clomiphene. In still other embodiments, the dopamine receptor agonist is selected from the group consisting of SKF81297, vanillyl-mandelic acid and dopamine. In additional embodiments, the alpha2-adrenergic receptor antagonist is rauwolscine. In still other embodiments the mGluR$_1$ antagonist is selected from the group consisting of AIDA, LY367385, and (S)-MCPG.

In another set of embodiments, the subject is free of symptoms otherwise calling for treatment with the composition.

According to another aspect of the invention, methods for treating a subject having a condition characterized by neuronal membrane depolarization are provided. The methods include administering to a subject in need of such treatment a composition selected from the group consisting of tyrosine kinase inhibitors, chloride channel antagonists, dopamine receptor agonists, alpha2-adrenergic receptor antagonists and mGluR$_1$ antagonists in an amount effective to reduce membrane depolarization, wherein the subject is free of symptoms otherwise calling for treatment with the composition. In some embodiments, the membrane depolarization is decreased to about 80% of its value in the absence of the composition. Preferably, the membrane depolarization is decreased to about 75% of its value in the absence of the composition. More preferably, the membrane depolarization is decreased to about 70% of its value in the absence of the composition. Still more preferably, the membrane depolarization is decreased to about 65% of its value in the absence of the composition. Most preferably, the membrane depolarization is decreased to about 60% of its value in the absence of the composition.

In certain embodiments, the tyrosine kinase inhibitor inhibits EGF receptor tyrosine kinase. Preferably the tyrosine kinase inhibitor is selected from the group consisting of 4,5-dianilinophthalimide (DAPH1) and tyrphostin 47. In other embodiments, the tyrosine kinase inhibitor inhibits TrkA receptor tyrosine kinase. Preferably such a tyrosine kinase inhibitor is tyrphostin AG879. In still other embodiments, the chloride channel antagonist is selected from the group consisting of nafoxidine and clomiphene. In still other embodiments, the dopamine receptor agonist is selected from the group consisting of SKF81297, vanillyl-mandelic acid and dopamine. In additional embodiments, the alpha2-adrenergic receptor antagonist is rauwolscine. In still other embodiments the mGluR$_1$ antagonist is selected from the group consisting of AIDA, LY367385, and (S)-MCPG.

According to still another aspect of the invention, compositions are provided that include one or more compounds that decrease membrane depolarization of neuronal cells caused by aggregated β-amyloid (Aβ) protein degradation products, and one or more compounds that decrease calcium influx of neuronal cells caused by aggregated β-amyloid (Aβ) protein degradation products. In some embodiments, the compositions also include a secretase inhibitor.

According to a further aspect of the invention, compositions are provided that include one or more compounds that decrease membrane depolarization of neuronal cells caused by aggregated β-amyloid (Aβ) protein degradation products, and a secretase inhibitor, or one or more compounds that decrease calcium influx in neuronal cells caused by aggregated β-amyloid (Aβ) protein degradation products, and a secretase inhibitor.

According to another aspect of the invention, methods for treating Alzheimer's disease are provided. The methods include administering an Aβ vaccine to a subject in need of such treatment, and administering to the subject an amount of a neuronal membrane depolarization inhibitor effective to inhibit membrane depolarization. Other methods include administering an Aβ vaccine to a subject in need of such treatment, and administering to the subject an effective amount of one or more of the compositions described above. Still other methods for treating Alzheimer's disease include administering to the subject an effective amount of one or more of the compositions described above.

According to a further aspect of the invention, methods for identifying lead compounds for a pharmacological agent useful in the treatment of conditions associated with increased neuronal depolarization induced by the presence of β-amyloid peptide (Aβ) aggregates are provided. The methods include providing a neuronal cell in a medium containing a potentiometric compound, wherein the influx into the neuronal cell of the potentiometric compound upon depolarization of the neuronal cell is detectable, contacting the neuronal cell with Aβ aggregates under conditions which permit influx of a control amount of the potentiometric compound into the neuronal cell, contacting the neuronal cell with a candidate pharmacological agent, and detecting the potentiometric compound in the neuronal cell as a measure of the relative depolarization of the neuronal cell in the presence of the candidate pharmacological agent. Detection of a lesser amount of potentiometric compound in the neuronal cell than is present when the neuronal cell is contacted with Aβ aggregates but not the candidate pharmacological agent indicates that the candidate pharmacological agent is a lead compound for a pharmacological agent which reduces Aβ aggregate induced neuronal cell depolarization.

In certain embodiments, the candidate pharmacological agent is a peptide or a small organic molecule. In other embodiments, the potentiometric compound is fluorescent. Preferably, the potentiometric compound is bis-(1,3-dibutylbarbituric acid)trimethine oxonol (DiBAC$_4$(3)).

In certain embodiments, the methods also include a control wherein the neuronal cell is not contacted with the Aβ aggregates, and/or a control wherein the neuronal cell is not contacted with the candidate pharmacological agent.

These and other objects and features of the invention are described in greater detail below.

DETAILED DESCRIPTION OF THE DRAWINGS

FIG. 1 shows that aggregated Aβ1–42 causes large membrane depolarization (A) and large calcium influx; and shows the effect of CNQX. FIG. 1A shows that fluorescence of the DiBAC$_4$(3) rose rapidly to a high plateau. The presence of CNQX, and replacing the buffer with Tyrode's/2Ca did not significantly change fluorescence. FIG. 1B shows that fluorescence of the ratiometric Ca dye fura-2 was converted to cytosolic calcium concentrations. In the presence of the aggregated Aβ1–42 there is a large increase in cytosolic calcium which spontaneously desensitizes to a level ~200% of control. Addition of CNQX lowers the remaining calcium level to the original control value.

FIG. 2 shows that tromethamine [TRIS$^+$] partially blocks membrane depolarization. hNT neuronal cells were exposed to aggregated 20 μM Aβ1–42 followed by Aβ1–42 plus 10 mM TRIS$^+$. The Tyrode's/2Ca buffer contained 100 nM DiBAC$_4$(3).

Figure 5:
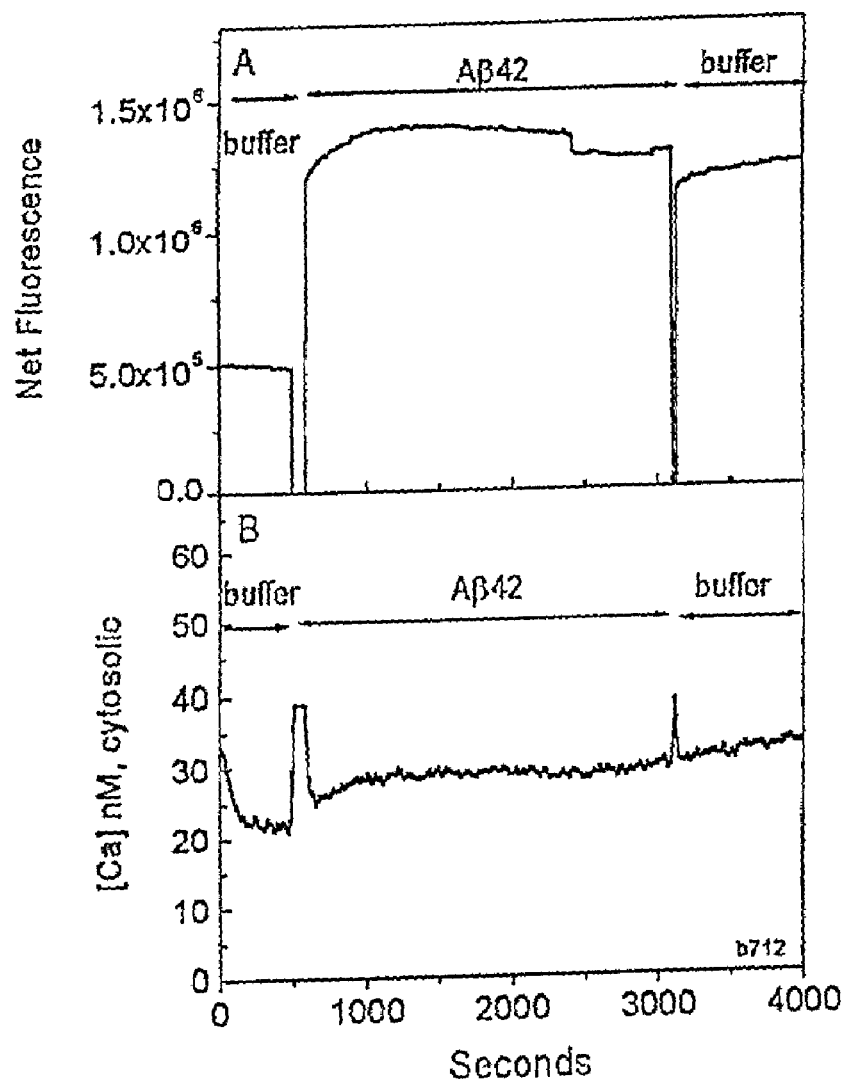

FIG. 5 shows the aggregated Aβ1–42 causes large membrane depolarization even when there is no calcium in the external solution. The hNT cells were exposed to aggregated Aβ1–42 in Tyrode's medium without calcium. FIG. 5A shows that the expected greatly increased membrane depolarization was observed as a plateau, lasting for ~2,500 seconds. FIG. 5B shows that there was almost no rise in cytosolic calcium.

Figure 6:
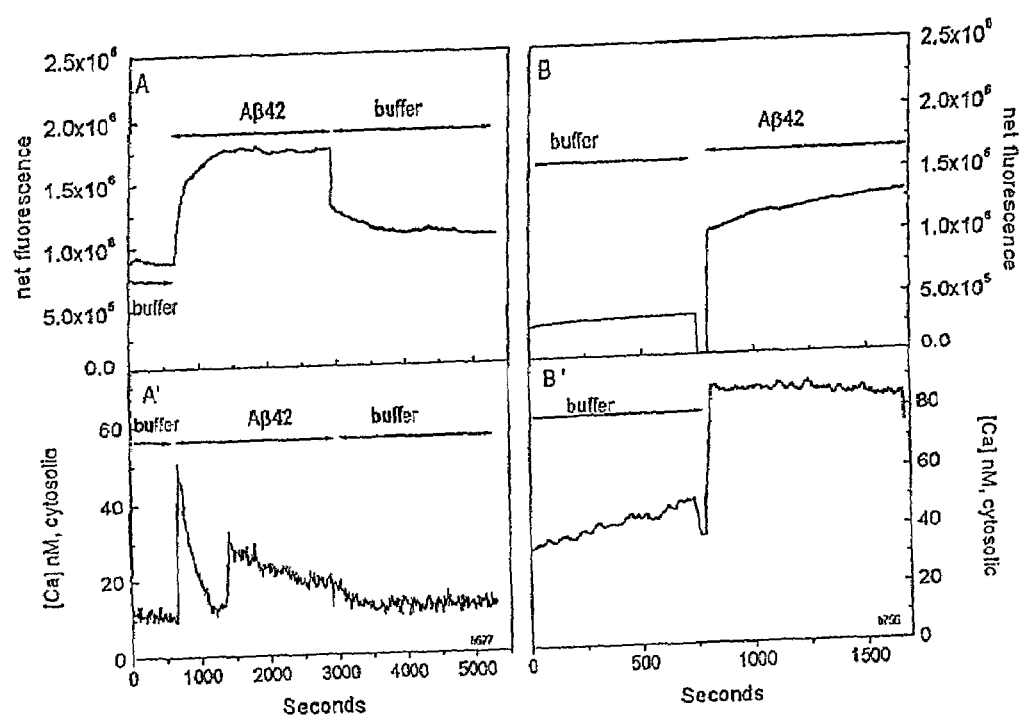

FIG. 6 indicates that sodium, the principal cation in the external buffer, can be replaced by the large cations TEA$^+$ and NMDG$^+$. FIGS. 6A and B show the changes in fluorescence of the voltage-sensitive dye DiBAC$_4$(3) and FIGS. 6A' and B' show changes in cytosolic calcium concentration, as measured by fura-2. FIG. 6A shows that replacing the external sodium ions with an equal concentration [150 mM] also allows a large and lasting membrane depolarization when aggregated Aβ1–42 is added to hNT cells. This is only partially reversed when the peptide solution is replaced with Tyrode's/2Ca. FIG. 6A' shows that the expected sharp increase in cytosolic calcium also occurs, followed by desensitization. The sharp dip and recovery of calcium levels is only seen in some experiments. FIG. 6B shows that when Na$^+$ in the external Tyrode's solution was replaced by the impermeant N-methyl-D-glucamine$^+$, membrane depolarization in the presence of aggregated Aβ1–42 was observed as usual. FIG. 6B' shows that cytosolic calcium also rises when aggregated Aβ1–42 is added.

Figure 7:
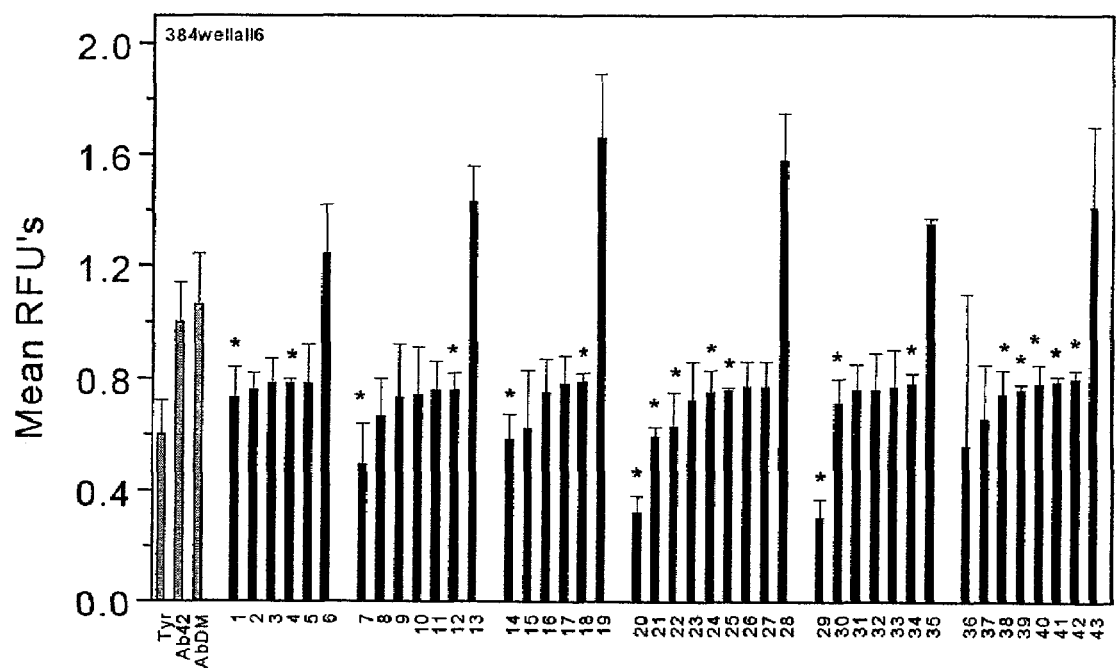

FIG. 7 depicts assays of Aβ1–42 induced membrane depolarization. Selected library compounds show a reduction in membrane depolarization caused by Aβ1–42 that gave values of <0.80 RFUs. Each column represents the mean RFU's of triplicate assays (five repeats for #1–6) for individual compounds. Each group represents one of six plates that comprised the single library of 1540 compounds. The last column of each group is the maximum mean value for that plate. The first three columns are the controls: Tyrode's2Ca, Aβ42, and Aβ42+DMSO, respectively. *=p<0.05

Figure 8:
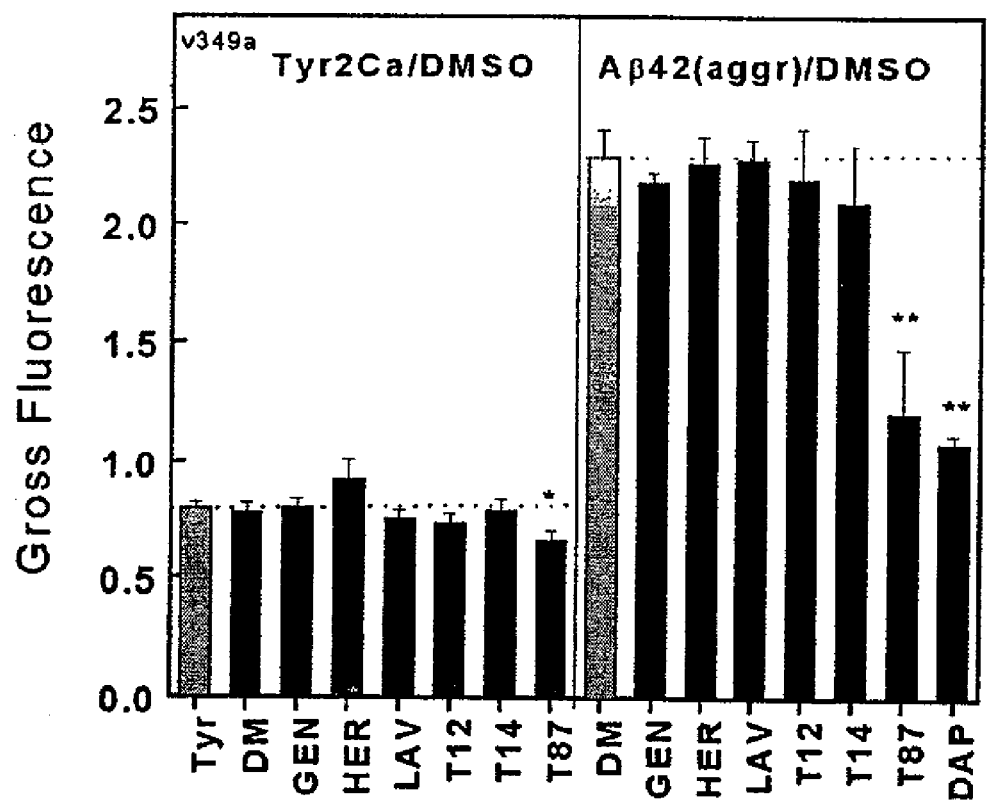

FIG. 8 shows characterization of "hit" compounds in multi-well tests. Seven tyrosine kinase inhibitors were tested for their ability to decrease membrane depolarization produced by aggregated Aβ1–42 [10 µM]. Compounds were also at 10 µM. The test compounds were dissolved in DMSO, final concentration=%. DM=DMSO; GEN=genistein; HER=herbimycin A; LAV=lavendustin A; T12=tyrphostin AG1295; T14=tyrphostin AG1478; T87=tyrphostin AG879; DAP=4,5-dianilinophthalimide (DAPH1); Ab=Aβ1–42; Tyr=Tyrode's/2Ca.

Figure 9:
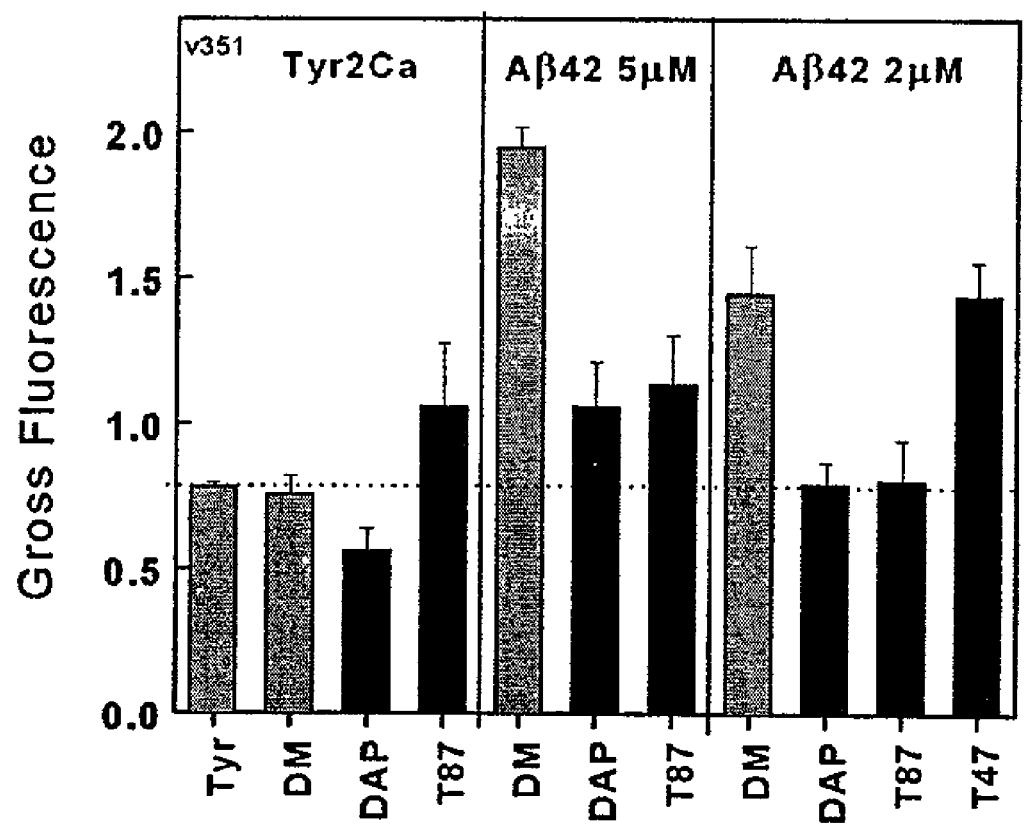

FIG. 9 depicts characterization of "hit" compounds at higher molar ratios in multi-well tests. Three tyrosine kinase inhibitors at 10 µM were tested for their ability to decrease membrane depolarization produced by aggregated Aβ1–42 at 5 µM and 2 µM. The test compounds were dissolved in DMSO, final concentration=%. DM=DMSO; T47=tyrphostin 47; T87=tyrphostin AG879; DAP=4,5-dianilinophthalimide (DAPH1); Ab=Aβ1–42; Tyr=Tyrode's/2Ca.

Figure 10:
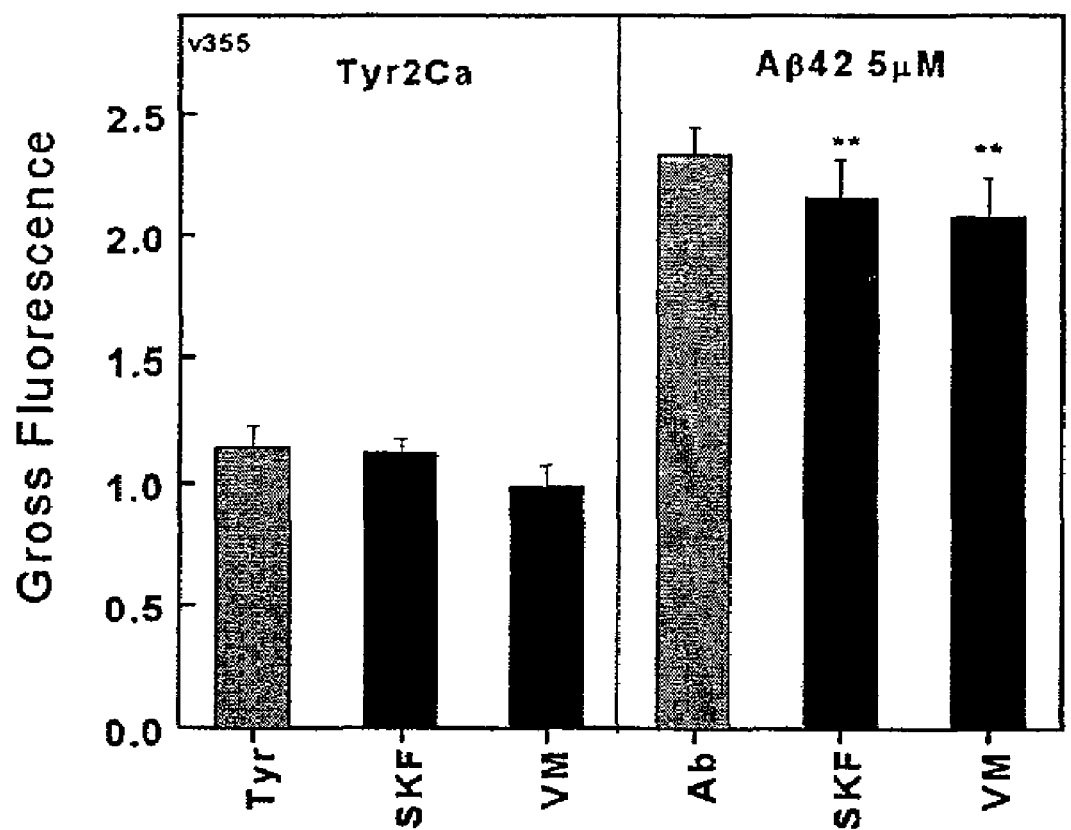

FIG. 10 shows the characterization of two dopamine agonists SKF81297 (6-Cl-PB) and VanillylMandelic Acid, producing hyperpolarization and reduction of Aβ1–42-induced depolarization. Tyr=Tyrode's/2Ca buffer; SKF=SKF81297 (6-Cl-PB) at 10 µM; VM=VanillylMandelic Acid at 10 µM; Ab5=Aβ1–42, aggregated at 5 µM.

Figure 11:
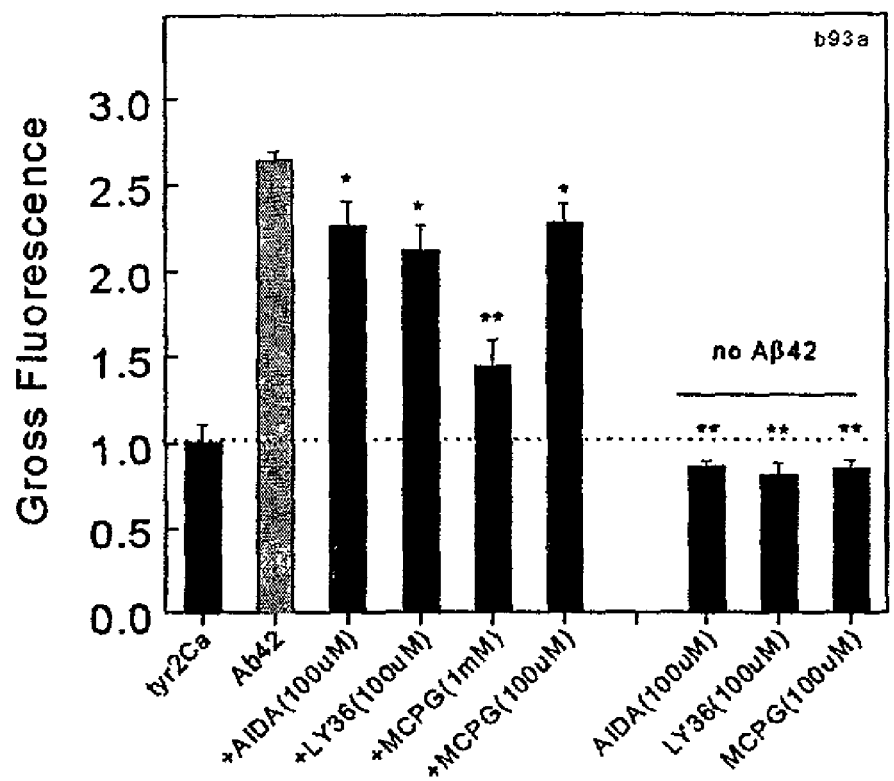

FIG. 11 depicts the effect of mGlu-receptor antagonists on Aβ-induced membrane depolarization. PC12 cells were pre-incubated for 30 minutes with various known mGlu receptor antagonists, and then exposed to pre-incubated Aβ1–42 at 10 µM. DiBAC4(3) was present at 97 nM, as usual. The changes in gross fluorescence are seen in the figure; *,** indicate differences from Aβ1–42aggr. alone at * p<0.05, ** p<<0.005.

DETAILED DESCRIPTION OF THE INVENTION

We have chosen the peptides Aβ25–35 (GSNKGAI-IGLM, SEQ ID NO:1) and Aβ1–42 (SEQ ID NO:2) as model systems to explore the effect of β-amyloid peptides on calcium homeostasis in neuronal cells, using quantitative estimation of the internal calcium concentration of the cells, and membrane depolarization, using voltage-sensitive fluorescent dyes.

Reports in the literature have shown that β-amyloid peptides cause an influx of calcium into cells, using not only Aβ25–35, but also Aβ1–40 (SEQ ID NO:3) and Aβ1–42. We have investigated the connection between β-amyloid peptide aggregation and the influx of calcium into neuronal cells as the first molecular event in the cytotoxicity of neurons in Alzheimer's Disease.

Pollard has reported the formation of ionophores from Aβ1–40 in artificial membrane which could be blocked by AlCl$_3$ or Tromethamine (Arispe, 1993). Our attempts to reproduce aluminum blockage in our experiments have been inconclusive because we found that AlCl$_3$ by itself powerfully induces calcium influx in hNT neuronal cells from external calcium sources. Thus, we turned to an alternative hypothesis, that aggregates of the β-amyloid peptides modulate ligand-gated ion channels such as NMDA and non-NMDA channels. Previous patch-clamp experiments indicated that voltage-gated calcium channels were not involved, because CdCl$_2$ did not block the calcium influx. We have also determined that the increased cytosolic calcium is derived entirely from the external medium. We have determined that calcium influx into hNT neuronal cells caused by Aβ25–35 can be blocked by MgCl$_2$, and by CNQX, but not by DL-AP5. hNT neuronal cells are known to express both NMDA and non-NMDA glutamate receptor channels. The blocking effect of CNQX, coupled with the lack of blocking effect of DL-AP5, indicated that the effect on calcium influx by Aβ25–35 aggregates in hNT cells is mediated by a non-NMDA cation channel. Since these observations involved the obligatory role of β-amyloid peptide aggregates, we hypothesized that compounds capable of antagonizing the formation of Aβ1–42 or Aβ25–35 aggregates will alleviate neurotoxicity of Alzheimer's Disease. These observations also suggest a strategy for developing therapeutics which modulate the activity of non-NMDA channels affected by β-amyloid peptide aggregates.

Peptides with a relatively high content of β-sheet forming sequence are likely to form multimers or aggregates, often in the form of fibrils, in aqueous solutions. Such β-sheet forming sequences are often present in intact globular proteins, but are embedded in other largely hydrophilic amino acid sequences and thus the proteins are kept in solutions. Once released from their precursor protein by proteolysis, peptides with β-sheet forming sequences can aggregate. Relevant to Alzheimer's Disease is the "abnormal" proteolysis of APP (Amyloid Precursor Protein) which yields Aβ1–40, Aβ1–42, and possibly also Aβ25–35. These peptides form aggregates, including fibrils, in aqueous solution which, as described above, may be causative agents of increased neuronal cell calcium influx.

Our aim was to design or select antagonistic peptides, which we call decoy peptides (DPs), which (i) reduce aggregate formation by either blocking aggregation of β-amyloid peptides or, by incorporation into the nascent aggregate, make it inactive; (ii) are soluble in aqueous solutions but retain β-sheet forming potential associated with the multimer-forming amyloid peptide; and (iii) contain amino acids with charged side chains that can interfere with the interaction between β-amyloid aggregates and ligand-gated $Ca^{2+}$ channels. Decoy peptides are unlikely to interact with β-sheet regions of other biologically important proteins because, as noted above, such regions generally are buried in the tertiary structure of the protein and therefore inaccessible. Preferably, decoy peptides are resistant to proteolytic digestion, to increase usefulness of such peptides in therapeutic applications. Decoy peptides active against β-amyloid neurotoxicity are described in U.S. Pat. No. 6,172,043.

It is believed that β-amyloid peptides are neurotoxic at least in part because they bind together to form multimers, or aggregates, which may even be fibrils of β-amyloid peptides linked together by binding of β-sheet structures of the β-amyloid peptides. Thus, compounds which prevent binding of β-amyloid peptides, which reduce the formation or size of the aggregates, such as fibrils, or which alter the tertiary structure and/or calcium influx or depolarization stimulating properties of the aggregates can be useful for reducing the neurotoxicity of β-amyloid peptides. It has been discovered that a certain class of peptides, decoy peptides, is effective in reducing neurotoxic β-amyloid peptide aggregate formation.

The invention thus involves in one aspect the discovery of a mechanism of β-amyloid peptide aggregate cytotoxicity, which in turn enables intervening to interfere with that aggregate cytotoxicity by administration of compounds which antagonize the mechanism of cytotoxicity. A number of compounds which antagonize the mechanism of cytotoxicity have been identified using the high-throughput methods of the invention. These compounds include organic molecules and inorganic molecules. In one aspect of the invention the compounds interfere with the ability of β-amyloid peptide to form neurotoxic aggregates, which aggregates cause unwanted cytotoxic calcium influx into cells. The compounds can affect neurotoxic aggregates by inhibiting binding of β-amyloid peptides to existing aggregates, by disrupting existing aggregates, by altering the structure of aggregates which incorporate the compound, by otherwise altering the structure of the aggregates (e.g. by capping) or by other mechanisms. Compounds useful in the invention also can interfere with unwanted calcium influx and/or membrane depolarization, e.g., by acting on the cell surface binding partner of the neurotoxic β-amyloid peptide aggregate, by reducing β-amyloid peptide aggregation, and the like. Examples of such compounds, discussed in greater detail below, include decoy peptides, which inhibit or interfere with neurotoxic β-amyloid peptide aggregates, and non-NMDA channel antagonists.

Various changes may be made to such compounds including the addition of various side groups that do not affect the manner in which the compound, e.g., decoy peptide, binds to its binding partner, or which favorably affect the manner in which the compound binds to its binding partner. Such changes may involve adding or subtracting charge groups, substituting amino acids, adding lipophilic moieties that do not effect binding but that affect the overall charge characteristics of the molecule facilitating delivery across the blood-brain barrier, etc. For each such change, no more than routine experimentation is required to test whether the molecule functions according to the invention. One simply makes the desired change or selects the desired compound and tests it in accordance with standard procedures as described herein. For example, if the candidate molecule interferes with the ability of a β-amyloid peptide to form neurotoxic aggregates that cause an increase in calcium influx, and/or alters membrane depolarization, in neuronal cells, then the candidate a decoy peptide or other compound useful in antagonizing the effects of β-amyloid aggregates.

As used herein, a "decoy peptide" is one which binds to a β-amyloid peptide, such as Aβ1–40, Aβ1–42, or Aβ25–35, and thereby reduces the ability of β-amyloid peptide to form neurotoxic aggregates. The decoy peptides may inhibit neurotoxic aggregate formation by inhibiting formation of new aggregates, inhibiting binding of β-amyloid peptides to existing aggregates, disrupting existing aggregates, altering the structure of aggregates which incorporate the decoy peptides or by other mechanisms. While not being limited to any particular mechanism, it is believed that decoy peptides can inhibit β-amyloid peptide aggregate formation by presenting a β-sheet secondary structure which is compatible with and binds to existing β-amyloid peptide β-sheet structures, but which does not permit binding of additional β-amyloid peptides sufficient to form aggregates. Alternatively, decoy peptides can inhibit β-amyloid peptide aggregate formation and/or cytotoxicity by altering the structure of the aggregate sufficiently to reduce its cytotoxic effects.

β-amyloid peptide aggregate formation can be determined directly, e.g., by observation of the extent of β-amyloid peptide aggregate formation by microscopy, or indirectly, e.g., by determination of the effects of β-amyloid peptide aggregate formation, such as a change in neuronal cell calcium influx or membrane depolarization. Other methods for determining the extent or effects of β-amyloid peptide aggregate formation will be apparent to one of ordinary skill in the art.

Compounds that reduce unwanted calcium influx induced by β-amyloid peptide aggregates also can be identifies. Calcium influx can be measured using indicator compounds which change a physical property (e.g., excitation/emission spectra) in response to a change in intracellular calcium concentration. Other methods for assaying changes in calcium influx useful in selecting compounds which oppose the effects of β-amyloid peptide aggregates on calcium influx will be known to one of ordinary skill in the art.

Still other methods for determining the effectiveness of a compound in inhibiting the neurotoxic effects of β-amyloid peptide aggregates can be used. For example, the effectiveness of compounds against damage in rat brain slices caused by neurotoxic β-amyloid peptide aggregates can be determined. As another example, Aβ fibrils can be injected into particular regions of rat brains to cause tissue damage which mimics the effects seen in Alzheimer's disease. Compounds can be administered to determine the sparing effect of the decoy peptides. All of the foregoing methods are known in the art and can be employed using no more than routine experimentation.

Compounds need not have both properties to be useful according to the invention. It is possible to identify compounds which do not inhibit β-amyloid peptide aggregation but do reduce β-amyloid-induced calcium influx or membrane depolarization, and vice versa. It is contemplated that compounds having only one of the desirable properties identified herein are useful, although it is preferable that a compound have more than one of such properties.

Selection of compounds which disrupt β-amyloid peptide aggregate formation is particularly contemplated. Methods for selecting such compounds include binding assays with which the art is familiar, as well as functional assays for determining the effects of such compounds on a biological response to aggregate formation, such as neuronal cell calcium influx. Methods for selecting compounds which disrupt β-amyloid peptide binding are provided in greater detail below.

Changes to the structure of a compound which disrupts β-amyloid peptide aggregate formation to form variants or analogs of such a compound can be made according to established principles in the art. Such changes can be made to increase the therapeutic efficacy of the compound, reduce side effects of the compound, increase or decrease the hydrophobicity or hydrophilicity, and the like. Changes to the structure include the addition of additional functional groups, such as for targeting the compound to a particular organ of a subject, and substitution of one or more portions of the compound. In general, substitutions involve conservative substitutions of particular moieties or subunits of the compound. For example, when preparing variants of a compound which is a peptide, one of ordinary skill in the art will recognize that conservative amino acid substitutions will be preferred, i.e., substitutions which retain a property of the original amino acid such as charge β-sheet forming potential, etc. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Preferred substitutions include substitutions amongst β-branched amino acids. Of course, non-conservative substitutions can also be made to the peptide sequence of the decoy peptides, followed by testing the function of the substituted decoy peptide as described herein.

Preferably, peptide-based compounds are non-hydrolyzable. To provide such peptide compounds, one may select peptides from a library of non-hydrolyzable peptides, such as peptides containing one or more D-amino acids or peptides containing one or more non-hydrolyzable peptide bonds linking amino acids. Alternatively, one can select peptides which are optimal for disrupting β-amyloid peptide aggregation, calcium influx and/or membrane depolarization and then modify such peptides as necessary to reduce the potential for hydrolysis by proteases. For example, to determine the susceptibility to proteolytic cleavage, peptides may be labeled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of a peptide with the known cleavage site specificity of a panel of proteases. Based on the results of such assays, individual peptide bonds which are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include -psi[$CH_2NH$]—reduced amide peptide bonds, -psi[$COCH_2$]—ketomethylene peptide bonds, -psi[CH(CN)NH]—(cyanomethylene)amino peptide bonds, -psi[$CH_2CH(OH)$]—hydroxyethylene peptide bonds, -psi[$CH_2O$]—peptide bonds, and -psi[$CH_2S$]—thiomethylene peptide bonds.

Peptides preferably are short enough to be synthesized and isolated readily, yet long enough to effectively disrupt β-amyloid peptide aggregate formation. Preferred peptides thus are between four and twenty amino acids in length, e.g., 4, 5, 6, 7, 8, 9, 10, 11, 12, 13, 14, 15, 16, 17, 18, 19, 20 amino acids. More preferably, peptides are between five and ten amino acids in length. Those skilled in the art are well-versed in methods for preparing and isolating such peptides, such as synthetic chemistry or even recombinant biological methods.

Peptides useful in the invention can be linear, or maybe circular or cyclized by natural or synthetic means. For example, disulfide bonds between cysteine residues may cyclize a peptide sequence. Bifunctional reagents can be used to provide a linkage between two or more amino acids of a peptide. Other methods for cyclization of peptides, such as those described by Anwer et al. (*Int. J. Pep. Protein Res.* 36:392–399, 1990) and Rivera-Baeza et al. (*Neuropeptides* 30:327–333, 1996) are also known to those of skill in the art.

Nonpeptide analogs of peptides, e.g., those which provide a stabilized structure or lessened biodegradation, are also contemplated. Peptide mimetic analogs can be prepared based on a selected decoy peptide by replacement of one or more residues by nonpeptide moieties. Preferably, the nonpeptide moieties permit the peptide to retain its natural confirmation, or stabilize a preferred, e.g., bioactive, confirmation. One example of methods for preparation of nonpeptide mimetic analogs from peptides is described in Nachman et al., *Regul. Pept.* 57:359–370 (1995). Peptide as used herein embraces all of the foregoing.

Decoy peptides are useful in the treatment of conditions which are characterized by β-amyloid peptide aggregate formation. Decoy peptides also are useful for the selection of other compounds which interfere with neurotoxic β-amyloid peptide aggregate formation, e.g., by use of a decoy peptide in competition assays to select compounds which bind to β-amyloid peptides more avidly than the decoy peptide and which still interfere with neurotoxic β-amyloid peptide aggregate formation. Decoy peptides are also useful in the design of other compounds for disrupting β-amyloid peptide aggregate formation, such as small molecule inhibitors, based on the molecular structure of the decoy peptide. Thus, the decoy peptides can be used in vivo for the treatment of disease, as well as in vitro for the design and testing of compounds active in the disruption of β-amyloid peptide aggregate formation.

In some circumstances, it may be preferred to conjugate the compound to a molecule which facilitates transport of the decoy peptide across the blood-brain barrier (BBB). As used herein, a molecule which facilitates transport across the BBB is one which, when conjugated to the compound, facilitates the amount of compound delivered to the brain as compared with non-conjugated compound. The molecule can induce transport across the BBB by any mechanism, including receptor-mediated transport, and diffusion. The compound can be conjugated to such molecules by well-known methods, including bifunctional linkers, formation of a fusion polypeptide, and formation of biotin/streptavidin or biotin/avidin complexes by attaching either biotin or streptavidin/avidin to the compound and the complementary molecule to the BBB-transport facilitating molecule.

Molecules which facilitate transport across the BBB include transferrin receptor binding antibodies (U.S. Pat. No. 5,527,527); certain lipoidal forms of dihydropyridine (see, e.g., U.S. Pat. No. 5,525,727); carrier peptides, such as cationized albumin or Met-enkephalin (and others disclosed in U.S. Pat. Nos. 5,442,043; 4,902,505; and 4,801,575); cationized antibodies (U.S. Pat. No. 5,004,697); and fatty acids such as docosahexanoic acid (DHA; U.S. Pat. No. 4,933,324).

For other uses of the compounds, it may be preferred to administer the compounds in combination with a molecule which increases transport of compounds across the blood-brain barrier (BBB). Such molecules, which need not be conjugated to a decoy peptide, increase the transport of the compound across the BBB into the brain. A molecule which increases transport across the BBB is one, for example, which increases the permeability of the BBB, preferably transiently. Coadministration of a compound with such a molecule permits the compound to cross a permeabilized BBB. Examples of such molecules include bradykinin and agonist derivatives (U.S. Pat. No. 5,112,596); and receptor-mediated permeabilizers such as A-7 (U.S. Pat. Nos. 5,268,164 and 5,506,206).

Compounds which reduce the ability of β-amyloid peptides to form aggregates which increase neuronal cell calcium influx and/or membrane depolarization can be administered to a subject to treat a condition characterized by unwanted β-amyloid peptide aggregates. Compounds are administered in an amount effective to reduce or inhibit formation of unwanted aggregates. By effective amount is meant an amount of a compound which inhibits formation of new unwanted β-amyloid peptide aggregates, modifies the structure of new or existing unwanted aggregates so that the aggregates do not increase neuronal cell calcium influx, or destabilizes existing unwanted aggregates. β-amyloid peptide aggregates can include one or more of Aβ1–42, Aβ1–40 and Aβ25–35, as well as other components.

Conditions characterized by unwanted β-amyloid peptide aggregate formation include Alzheimer's Disease. It will be apparent to one of ordinary skill in the art that cytotoxicity of certain neuronal cells is involved in such conditions. For example, neuronal cells involved in Alzheimer's Disease include cells from hippocampal neurons, cortical layer 3 neurons, amygdala neurons, locus coeruleus neurons, and others known to be involved in memory formation and storage. It is envisioned that the compounds described herein, particularly decoy peptides, can be delivered to neuronal cells by site-specific means. Cell-type-specific delivery can be provided by conjugating a compound to a targeting molecule, e.g., one which selectively binds to the affected neuronal cells. Methodologies for targeting include conjugates, such as those described in U.S. Pat. No. 5,391,723 to Priest. Another example of a well-known targeting vehicle is liposomes. Liposomes are commercially available from Gibco BRL. Numerous methods are published for making targeted liposomes. Liposome delivery can be provided by encapsulating a decoy peptide in liposomes which include a cell-type-specific targeting molecule. Methods for targeted delivery of compounds to particular cell types are well-known to those of skill in the art.

Methods for reducing β-amyloid peptide induced neuronal cell calcium influx also are provided. The internal calcium concentration in neuronal cells can be affected by release of calcium from intracellular stores, influx of calcium from the extracellular milieu and possibly other sources. As described herein β-amyloid peptides increase internal calcium concentrations by influencing the permeability of certain ligand-gated ion channels, the non-NMDA channels. Non-NMDA channels are ordinarily activated by a combination of two factors: (1) the presence of the excitatory amino acid neurotransmitter glutamate, and (2) a lack of magnesium ions at the cell surface following depolarization of the cell. Non-NMDA channels include subtypes for which AMPA ((RS)-2-amino-3-(3-hydroxy-5-methyl-isoxazol-4-yl)-propionate) and kainate are agonists.

The discovery of a calcium influx mechanism by which β-amyloid peptides induce neurotoxicity provides a basis for treating conditions characterized by β-amyloid peptide induced calcium influx. Thus, subjects can be treated by administering any compounds which reduce the β-amyloid peptide induced calcium influx. Such compounds can be inorganic or organic and can act on the β-amyloid peptide, the neurotoxic β-amyloid peptide aggregate or the cell surface binding partner of the neurotoxic β-amyloid peptide aggregate to interfere with unwanted calcium influx. Examples of such compounds include decoy peptides which inhibit or interfere with neurotoxic β-amyloid peptide aggregates, and non-NMDA channel antagonists. The compounds are administered in an effective amount, i.e., an amount which reduces the increased calcium influx. In neuronal cell types other than NT2-N cells differentiated with retinoic acid β-amyloid peptides may induce neurotoxicity via calcium influx through other means, such as NMDA channels. It is contemplated, therefore, that antagonists of calcium channels other than non-NMDA channels can be administered to treat conditions characterized by β-amyloid peptide induced calcium influx.

Non-NMDA channel antagonists are well-known in the art. Such antagonists inhibit the calcium influx by inhibiting the opening of a non-NMDA channel in response to its ligand, such as glutamate, AMPA, kainate or, according to the invention, neurotoxic β-amyloid peptide aggregates. Non-NMDA channel antagonists can act competitively or noncompetitively, and can block one or more subtypes of non-NMDA channels. Preferably, antagonists used are those which inhibit the function of only those channels opened by β-amyloid peptide aggregates. Useful non-NMDA antagonists include 6-cyano-7-nitroquinoxaline-2,3-dione (CNQX), 6,7-dinitroquinoxaline-2,3(1H, 4H)-dione (DNQX), 2,3-dihydroxy-nitro-7-sulfamoyl-benzo[f]quinoxaline (NBQX), 1-(4-chlorobenzoyl)piperazine-2,3-dicarboxylic acid (CBPD), 6,7-dichloro-2(1H)-oxoquinoline-3-phosphonic acid (24c), Evans blue, 2,3-dihydroxy-7-sulfamoyl-benzo[f]quinoxaline (BQX), derivatives of 4-oxo-1,4-dihydroquinoline-2-carboxylic acid at the 6-position, 2-amino-3-[3-(carboxymethoxy)-5-methylisoxazol-4-yl]propionic acid (AMOA), 2-amino-3-[2-(3-hydroxy-5-methylisoxazol-4-yl)-methyl-5-methyl-3-+++ oxoisoxazolin-4-yl]propionic acid (AMNH), 1-(4-aminophenyl)-4-methyl-7,8-methyl-endioxyl-5H-2,3-benzodiazepine (GYKI 52466), 6-(1H-imidazol-1-yl)-7-nitro-2,3(1H,4H)-quinoxalinedione hydrochloride (YM90K), 1-(4-aminophenyl)-3-methylcarbamyl-4-methyl-7,8-methylenedioxy-3,4 -dihydro-5H-2,3-benzodiazepine (GYKI 53655), and (−)(3S,4aR,6R,8aR)-6-[2-(1(2)H-tetrazole-5-yl)ethyl]-1,2,3,4,4a,5,6,7,8,8a-decahydroisoquinoline-3-carboxylic acid monohydrate (LY326325).

Likewise, the discovery of a membrane depolarization mechanism by which β-amyloid peptides induce neurotoxicity provides a basis for treating conditions characterized by β-amyloid peptide induced membrane depolarization. Thus, subjects can be treated by administering any compounds which reduce the β-amyloid peptide induced membrane depolarization. Such compounds can be inorganic or organic and can act on the β-amyloid peptide, the neurotoxic β-amyloid peptide aggregate or the cell surface binding partner of the neurotoxic β-amyloid peptide aggregate to interfere with unwanted membrane depolarization. Exemplary compounds that decrease β-amyloid peptide aggregate induced membrane depolarization are identified in the Examples.

The invention further provides efficient methods of identifying pharmacological agents or lead compounds for agents useful in the treatment of conditions associated with β-amyloid peptide aggregation or conditions associated with increased neuronal cell calcium influx induced by the presence of β-amyloid peptide aggregates. Generally, the screening methods involve assaying for compounds which interfere with β-amyloid peptide aggregation or neuronal cell calcium influx through non-NMDA channels as regulated by β-amyloid peptide aggregates. Such methods are adaptable to automated, high throughput screening of compounds.

A wide variety of assays for pharmacological agents are provided, including, labeled in vitro peptide-peptide binding assays, $Ca^{2+}$ influx assays, etc. For example, peptide binding screens are used to rapidly examine the effect of candidate pharmacological agents on the binding of decoy peptides to β-amyloid peptide. The candidate pharmacological agents can be derived from, for example, combinatorial peptide libraries. Convenient reagents for such assays are known in the art. An exemplary cell-based assay involves contacting a neuronal cell with a mixture of β-amyloid peptide and a candidate pharmacological agent. A reduction in the induction of calcium influx by resulting β-amyloid peptide aggregates indicates that the candidate pharmacological agent disrupts β-amyloid peptide aggregate formation or reduces the sensitivity of calcium channels to β-amyloid peptide aggregates. Methods for determining changes in the intracellular calcium concentration are known in the art and are addressed elsewhere herein.

β-amyloid peptides used in the methods of the invention are added to an assay mixture as an isolated peptide. β-amyloid peptides can be produced recombinantly, or isolated from biological extracts, but preferably are synthesized in vitro. β-amyloid peptides encompass chimeric proteins comprising a fusion of a β-amyloid peptide with another polypeptide, e.g., a polypeptide capable of providing or enhancing protein-protein binding, or enhancing stability of the β-amyloid peptide under assay conditions. A polypeptide fused to a β-amyloid peptide or fragment may also provide means of readily detecting the fusion protein, e.g., by immunological recognition or by fluorescent labeling.

The assay mixture includes a β-amyloid peptide, such as Aβ1–42, Aβ1–40, and Aβ25–35 and can include a decoy peptide as described herein.

The assay mixture also comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate pharmacological agents are small organic compounds, i.e., those having a molecular weight of more than 50 yet less than about 2500. Candidate agents comprise functional chemical groups necessary for structural interactions with polypeptides, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids having non-natural bonds or subunits are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease, inhibitors, nuclease inhibitors, antimicrobial agents, and the like may also be used.

The mixture of the foregoing assay materials is incubated under conditions whereby, but for the presence of the candidate pharmacological agent, the β-amyloid peptide forms aggregates and specifically binds the cellular binding target and induces neuronal calcium influx, and/or induces membrane depolarization. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 1 minute and 10 hours.

After incubation, the presence or absence of specific binding between the β-amyloid peptide and one or more binding partners is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximum signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as a calcium influx assay. The calcium influx resulting from β-amyloid peptide aggregation and binding to a target molecule typically alters a directly or indirectly detectable product, e.g., a calcium sensitive molecule such as fura-2-AM. For cell free binding assays, one of the components usually comprises, or is coupled to, a detectable label. A wide variety of labels can be used, such as those that provide direct detection (e.g., radioactivity, luminescence, optical or electron density, etc). or indirect detection (e.g., epitope tag such as the FLAG epitope, enzyme tag such as horseradish peroxidase, etc.). The label may be bound to a β-amyloid peptide, decoy peptide or the candidate pharmacological agent.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

Thus the present invention includes automated drug screening assays for identifying compositions having the ability to inhibit ion influx in a cell induced by Aβ aggregates, thus contributing to a detectable change in the cytoplasmic level of a predetermined ion in the cell, the cytoplasm of which cell contains an indicator which is sensitive to the ion. The method is carried out in an apparatus which is capable of delivering a reagent solution to a plurality of predetermined cell-containing compartments of a vessel and measuring the detectable change in the cytoplasmic level of the ion in the cells of the predetermined compartments, such as the apparatus and method described in U.S. Pat. No. 6,057,114. Exemplary methods include the following steps. First, a divided culture vessel is provided that has one or more compartments which contain viable cells which, when exposed to Aβ aggregates, have a detectable change in the concentration of the predetermined ion in the cytoplasm. The cytoplasms of the cells include an amount of an ion-sensitive fluorescent indicator sufficient to detect a change, if any, in the concentration of the predetermined ion. Aβ aggregates are added to the cells to induce calcium influx and/or depolarization. Next, one or more predetermined cell-containing compartments are aligned with a predetermined position (e.g., aligned with a fluid outlet of an automatic pipette) and an aliquot of a solution containing a compound or mixture of compounds being tested for its ability to modulate Aβ fibril-induced calcium influx and/or depolarization is delivered to the predetermined compartment(s) with an automatic pipette. Finally, fluorescence emitted by the ion-sensitive indicator in response to an excitation wavelength is measured for a predetermined amount of time, preferably by aligning said cell-containing compartment with a fluorescence detector. Preferably, fluorescence also measured prior to adding Aβ aggregates to the cells and/or prior to adding the compound to the wells, to establish e.g., background and/or baseline values for fluorescence.

In accordance with the various assays of the present invention, cells are employed which have ion channels and/or receptors, the activation of which by aggregated Aβ peptides (i.e., Aβ aggregates or fibrils) results in a change in the level of a cation or anion in the cytoplasm. The cytoplasm of the cells employed are loaded with a fluorescent indicator which is sufficiently sensitive to said ion. By the phrase "sufficiently sensitive fluorescent indicator" is meant a fluorescent compound which, in the presence of, and over a range of physiological concentrations of, a particular ion, is capable of producing distinguishable levels of fluorescence intensity. Preferably, a fluorescent indicator should be able to produce detectably different intensities of fluorescence in response to relatively small changes in ion concentration. The relative intensities of fluorescence when the receptors or ion channels have not been activated, as compared to when the receptors or ion channels have been activated, preferably differ by at least about 50% or more, more preferably by at least about 100–200%.

Any cell which is capable, upon exposure to Aβ aggregates, of directly increasing the intracellular concentration of calcium, such as by permitting calcium influx through calcium channels or ion pores formed in accordance with the ionophore properties of Aβ aggregates, or by causing release of calcium from intracellular stores, may be used in the assay. Preferably neuronal cell lines or cultured neurons are used. Such cells include, but are not limited to, the hNT neuronal cells used in the Examples.

Activation of cellular receptors and/or ion channels (e.g., AMPA/kainate-type channels) by incubation with Aβ aggregates and/or ionophore formation by Aβ aggregates, may result in a transient increase in the level of intracellular calcium (and/or other ions). The initial increase in calcium may be detected as a rapid increase in fluorescence (e.g., within one to two seconds) after the addition of the Aβ aggregates. As shown herein, calcium influx is generally short-lived, but depolarization is longer lasting. Fluorescence levels in the cytoplasm resulting from calcium influx typically increase to a peak value and then typically decline as excess calcium ions are removed by normal cellular mechanisms. Fluorescence due to depolarization after Aβ fibril exposure rapidly increases to a plateau value, and remains at this plateau. The speed at which the fluorescence can be analyzed is important for analysis of the kinetics of the reaction, if it is desired to measure kinetics.

The cells used in the assays of the invention are loaded with a fluorescent indicator which is sufficiently sensitive so as to produce detectable changes in fluorescence intensity in response to changes in the concentration of the ions in the cytoplasm. It is particularly preferred to use a fluorescent indicator which has such sensitivity in the presence of calcium ions, although indicators sensitive to other ions such as sodium ions, potassium ions, chloride ions, and the like may be employed depending on the type of ion flux induced by the Aβ aggregates, as will be understood by the person of ordinary skill in the art. Among the fluorescent indicators which may be employed are the following compounds commercially available from, e.g., Molecular Probes, Inc., Eugene Oreg.: DiBAC$_4$(3) (B-438), Quin-2 (AM Q-1288), Fura-2 (AM F-1225), Indo-1 (AM I-1226), Fura-3 (AM F-1228), Fluo-3 (AM F-1241), Rhod-2, (AM R-1244), BAPTA (AM B-1205), 5,5'-dimethyl BAPTA (AM D-1207), 4,4'-difluoro BAPTA (AM D-1216), 5,5'-difluoro BAPTA (AM D-1209), 5,5'-dibromo BAPTA (AM D-1213), Calcium Green (C-3011), Calcium Orange (C-3014), Calcium Crimson (C-3017), Fura-5 (F-3023), Fura-Red (F-3020), SBFI (S-1262), PBFI (P-1265), Mag-Fura-2 (AM M-1291), Mag-Indo-1 (AM M-1294), Mag-Quin-2 (AM M-1299), Mag-Quin-1 (AM M-1297), SPQ (M-440), and SPA (S-460).

It is contemplated that each of the individual wells contain the same cell type so that multiple compounds (obtained from different reagent sources in the apparatus or contained within different wells) can be screened and compared for modulating activity with respect to Aβ fibril-induced calcium influx and/or depolarization.

In another of its aspects the invention entails automated antagonist assays. Antagonist assays, including drug screening assays, may be carried out by incubating the cells (e.g., neurons) with Aβ aggregates to induce calcium influx and/or depolarization, in the presence is and absence of one or more compounds added to the solution bathing the cells in the respective wells of the microtiter plate for an amount of time sufficient for the compound(s) to modulate calcium influx and/or depolarization, and measuring the level of fluorescence in the cells as compared to the level of fluorescence in either the same cell, or substantially identical cell, in the absence of the Aβ aggregates.

As will be understood by the person of ordinary skill in the art, compounds exhibiting agonist or antagonist activity in an assay of calcium influx or depolarization will either increase or decrease intracellular ion levels (agonist) or inhibit (antagonist) an increase or decrease in the intracellular concentration of ions after incubation of cells with Aβ aggregates. It is desirable to measure the amount of agonist or antagonist activity in a linear range of the assay system, such that small but significant increases or decreases in fluorescence relative to control well (e.g., devoid of the test compound) may be observed. It is well within the skill of the art to determine a volume and concentration of a reagent solution which causes a suitable activation response in cells so that modulation of the calcium influx and/or depolarization may be reliably detected.

At a suitable time after addition of the Aβ aggregates to initiate calcium influx and/or depolarization, the plate is moved, if necessary, so that the cell-containing assay well is positioned for measurement of fluorescence emission. Because a change in the fluorescence signal may begin within the first few seconds after addition of test compounds, it is desirable to align the assay well with the fluorescence reading device as quickly as possible, with times of about two seconds or less being desirable. In preferred embodiments of the invention, where the apparatus is configured for detection through the bottom of the well(s) and compounds are added from above the well(s), fluorescence readings may be taken substantially continuously, since the plate does not need to be moved for addition of reagent. The well and fluorescence-reading device should remain aligned for a predetermined period of time suitable to measure and record the change in intracellular ion, e.g., calcium, concentration. In preferred embodiments of the invention the fluorescence after activation is read and recorded until the fluorescence change is maximal and then begins to reduce. An empirically determined time period may be chosen which covers the transient rise and fall (or fall and rise) of intracellular ion levels in response to addition of the compound. When the apparatus is configured to detect fluorescence from above the plate, it is preferred that the bottom of the wells are colored black to reduce the background fluorescence and thereby decreases the noise level in the fluorescence reader.

After finishing reading and recording the fluorescence in one well, the just described apparatus steps are repeated with the next well(s) in the series so as to measure pre-reagent fluorescence, add reagent and measure and record the transient change, if any, in fluorescence. The apparatus of the present invention is programmable to begin the steps of an assay sequence in a predetermined first well (or row or column of wells) and proceed sequentially down the columns and across the rows of the plate in a predetermined route through well number n.

In assays of cells treated with Aβ aggregates to cause an increase in intracellular calcium ion concentration and/or depolarization, it is preferred that the fluorescence data from replicate wells of cells treated with the same compound are collected and recorded (e.g., stored in the memory of a computer) for calculation of fluorescence and/or intracellular calcium ion concentration.

In assays of compounds that inhibit calcium influx and/or depolarization, the results can be expressed as a percentage of the maximal response caused by Aβ aggregates (e.g., Aβ1–42 aggr.). The maximal fluorescence increase caused by Aβ aggregates is defined as being 100% response. For compounds effective for reducing calcium influx and/or depolarization induced by Aβ aggregates, the maximal fluorescence recorded after addition of a compound to wells containing Aβ aggregates is detectably lower than the fluorescence recorded in the presence of only Aβ aggregates.

The fluorescence indicator-based assays of the present invention are thus useful for rapidly screening compounds to identify those that modulate calcium influx and/or depolarization that ultimately results in an altered concentration of ions in the cytoplasm of a cell. For example, the assays can be used to test functional ligand interactions with Aβ aggregates or ligand competition with decoy peptide binding of Aβ aggregates.

Automation of the fluorescent dye-based assays of the invention can be performed as described in U.S. Pat. No. 6,057,114. Automation can provide increased efficiency in conducting the assays and increased reliability of the results by permitting multiple measurements over time, thus also facilitating determination of the kinetics of the calcium influx or depolarization effects.

For example, to accomplish rapid compound addition and rapid reading of the fluorescence response, the fluorometer can be modified by fitting an automatic pipetter and developing a software program to accomplish precise computer control over both the fluorometer and the automatic pipetter. By integrating the combination of the fluorometer and the automatic pipetter and using a microcomputer to control the commands to the fluorometer and automatic pipetter, the delay time between reagent addition and fluorescence reading can be significantly reduced. Moreover, both greater reproducibility and higher signal-to-noise ratios can be achieved as compared to manual addition of reagent because the computer repeats the process precisely time after time. Moreover, this arrangement permits a plurality of assays to be conducted concurrently without operator intervention. Thus, with automatic delivery of reagent followed by multiple fluorescence measurements, reliability of the fluorescent dye-based assays as well as the number of assays that can be performed per day are advantageously increased.

The invention, in one aspect, identifies compounds which reduce the increased neuronal cell membrane depolarization induced by the presence of β-amyloid peptide aggregates., methods of identifying and making such agents, and their use in diagnosis, therapy and pharmaceutical development. These compounds are useful in a variety of diagnostic and therapeutic applications, especially where disease or disease prognosis is associated with improper utilization of a pathway involving β-amyloid peptide, e.g. β-amyloid peptide aggregation, neuronal membrane depolarization associated with neurotoxic β-amyloid peptide aggregates, etc.

Compounds which antagonize the formation of neurotoxic β-amyloid peptide aggregates or which inhibit calcium influx and/or membrane depolarization may be administered as part of a pharmaceutical composition. Such a pharmaceutical composition may include the compounds in combination with any standard physiologically and/or pharmaceutically acceptable carriers which are known in the art. The compositions should be sterile and contain a therapeutically effective amount of the therapeutic compound in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

When used therapeutically, the compounds of the invention are administered in therapeutically effective amounts. In general, a therapeutically effective amount means that amount necessary to delay the onset of, inhibit the progression of, or halt altogether the particular condition being treated. Therapeutically effective amounts specifically will be those which desirably influence the existence or formation of aggregates of β-amyloid peptides that induce calcium influx in neuronal cells, and/or desirably influence the cytotoxic effects of such aggregates. Generally, a therapeutically effective amount will vary with the subject's age, and condition, as well as the nature and extent of the disease in the subject, all of which can be determined by one of ordinary skill in the art. The dosage may be adjusted by the individual physician, particularly in the event of any complication. A therapeutically effective amount typically varies from 0.01 mg/kg to about 1000 mg/kg, preferably from about 0.1 mg/kg to about 200 mg/kg and most preferably from about 0.2 mg/kg to about 20 mg/kg, in one or more dose administrations daily, for one or more days.

The therapeutics of the invention can be administered by any conventional route, including injection or by gradual infusion over time. The administration may, for example, be oral, intravenous, intracranial, intraperitoneal, intramuscular, intracavity, intrarespiratory, subcutaneous, or transdermal. The route of administration will depend on the composition of a particular therapeutic preparation of the invention.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. Such implants can be particularly useful in treating conditions characterized by aggregates of β-amyloid peptides by placing the implant near portions of the brain affected by such aggregates, thereby effecting localized, high doses of the compounds of the invention.

EXAMPLES

Example 1

Aβ1–42 Aggregates Increase Neuronal Cell Depolarization

Aβ1–42 Sample Preparation

Aβ1–42 was obtained from Quality Controlled Biochemicals, Inc. (Hopkinton, Mass.). Two particular batches of the peptide were used. A stock solution of Aβ1–42 (1 mM) was made in double-distilled, deionized water adjusted to pH 9 with 1M ammonium hydroxide and stored in aliquots at −40° C. until use. Experimental samples were prepared by diluting stock Aβ1–42 to 10 μM (unless otherwise noted) in Tyrode's/2 mMCa buffer (pH 7.4).

Membrane Potential Measurements

Changes in membrane potential were measured using the fluorescent potentiometric probe DiBAC$_4$(3), (Molecular Probes, Inc., Eugene, Oreg.). This dye, bis-(1,3-dibutylbarbituric acid)trimethine oxonol, detects membrane depolarization, because it enters depolarized cells and binds to intracellular proteins or membranes. The bound dye exhibits enhanced fluorescence and red spectral shift (Hartinger and Jahn, *J. Biol. Chem* 268:23122–23127, 1993; Cooper et al., *Biochemistry* 29:3859–3865, 1990). Hyperpolarization results in extrusion of the anionic dye and thus a decrease in fluorescence.

The bis-oxonol dye DiBAC$_4$(3) was used as an indicator of transmembrane electrical potential changes (Langheinrich and Daut, *J. Physiol.* 502:397–408, 1997) in neuronal cells such as the undifferentiated PC12 cells treated with aggregated Aβ1–42 β-amyloid peptide. The use of this dye enabled us to monitor groups of 5–15 neurons, rather than single cells as would be the case with patch clamping methods. We expected great variability from cell to cell, as was found in our earlier patch clamp work (Sanderson et al., *Brain Res.* 744:7–14, 1997). The method has been used by many laboratories for the determination of membrane potentials in different cell types. Fluorescence is increased upon membrane depolarization as more dye enters the cytosol, resulting in increased binding to proteins (Bräuner et al., *Biochim. Biophys. Acta* 771:2208–216, 1984). Partitioning of bis-oxonol dye between the plasma membrane and the cytosol follows the Nernst equation (Langheinrich and Daut, 1997). Unless otherwise indicated, all measurements were carried out in Tyrode's solution containing 2 mM Ca.

We calibrated the gross fluorescence as a function of membrane potential by treating a culture of hNT neurons, bathed in Tyrode's 2Ca buffer with the usual 3 mM $K^+$, containing 97 nM $DiBAC_4(3)$, with Tyrode's 2Ca buffer containing 40 mM KCl. We measured the gross fluorescence at excitation=490 nm and emission=510 nm for the depolarization by KCl and for depolarization by the Aβ1–42 peptide. We used the formula proposed by Langheinrich and Daut, 1997:

$$\%\Delta F = (1 - F_{min}/F_{max})*100 = \Delta E_M \text{mV}$$

where $F_{min}$=fluorescence before treatment, $F_{max}$=fluorescence during treatment, $\Delta E_M$ mV is the change in membrane potential brought about by the treatment. The calculation based on the expected depolarization by changing from 3 mM KCl to 40 mM KCl gave a value of $\Delta E_M$=3.8 mV/1% $\Delta F$.

96-Well-Plate Experiments

Undifferentiated rate pheochromocytoma cells, PC12 cells from ATCC #CRL-1721 or from other sources, were cultured in 96-well black/clear plates (VWR #35–6640) coated with poly-D-lysine. Each reagent mixture was measured in 3–4 parallel wells. Cell density at the time of plating (~5×10$^4$ per well/100 μl) was sufficient to produce a confluent or nearly confluent cell layer within 1–3 days.

Growth medium (RPMI, 10% horse serum, 5% fetal bovine serum, 1% L-glutamine, 1% pen-strep) was removed using a multi-pipetter and the cells were washed with 100 μl/well of Tyrode's/2Ca buffer, pH 7.4. Test solutions contained 97 nM $DiBAC_4(3)$ (Molecular Probes, Eugene, Oreg.). Measurements were taken after 15 min at RT with the Fluoroskan II (LabSystems, Franklin, Mass.); $E_X$=485 nm, $E_m$=510 or 538 nm. Changes in gross fluorescence as %ΔF were calculated, as described above.

To measure the β-sheet formation, thioflavin T (ThT; final concentration 5 μM) was added to each seed-free Aβ1–42 sample in Tyrode's/2Ca, pH 7.4, following incubation. Ninety μl of each sample was pipetted into each of three wells in a 96-well black, flat-bottomed plate (VWR #35–3943). ThT fluorescence was measured in a Fluoroskan II fluorometer at room temperature; $E_X$=444 nm, $E_m$=510 nm. Each well was measured four times in quick succession. The readings were stable.

Aggregated Aβ1–42 Induces Membrane Depolarization

Figure 1:
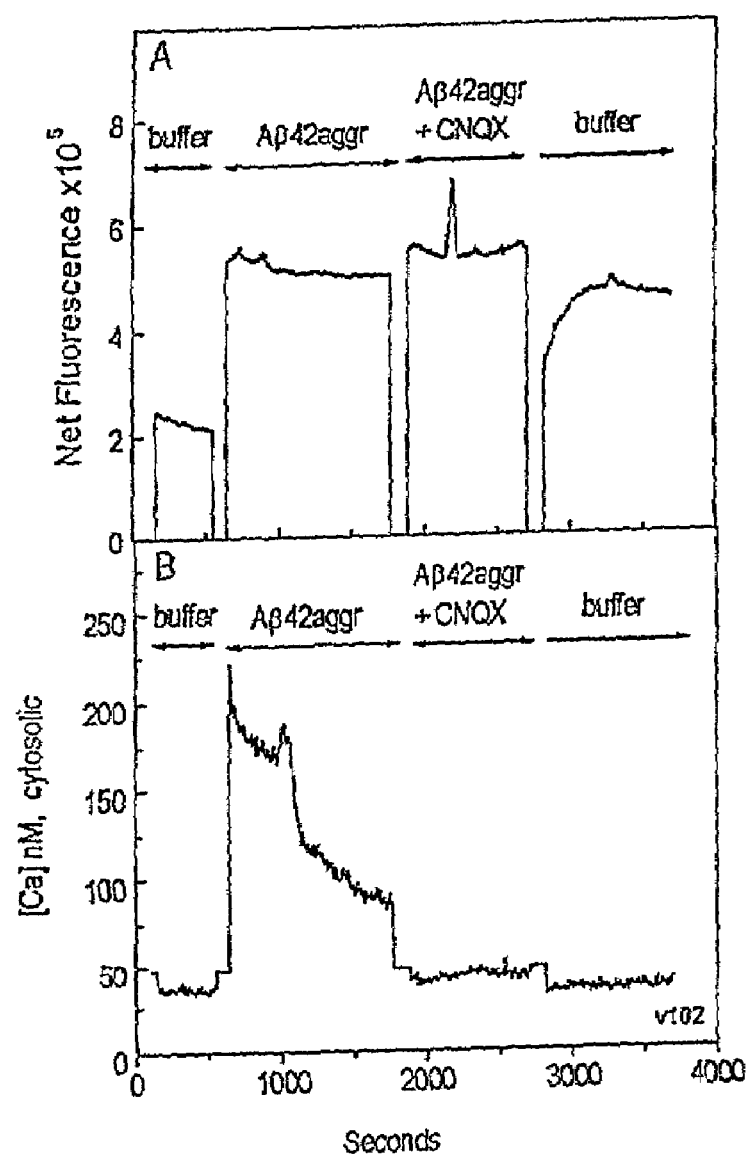

Addition of the pre-aggregated Aβ1–42 β-amyloid peptide (Aβ1–42aggr) to cultured hNT neuronal cells caused a large membrane depolarization in the cells. Groups of hNT cells, loaded with fura-2 and in Tyrode's/2Ca buffer containing $DiBAC_4(3)$, were exposed to aggregated Aβ1–42 for approximately 1,200 seconds. In the presence of the slow-acting voltage-sensitive fluorescent dye $DiBAC_4(3)$, there was an immediate sharp increase in fluorescence to a high plateau when Aβ1–42aggr was added (FIG. 1A), indicating cell membrane depolarization. The new plateau was moderately stable for at least 1,000 seconds, and often longer, but fluctuations sometimes were observed. CNQX, an AMPA/kainate antagonist, was then added and was also present for the next ~1,000 seconds. Gross fluorescence increased on average by 17%, which corresponded to an increase in membrane potential of ~64 mV. There was little change in fluorescence; the sharp peak in fluorescence is unexplained. Replacing the buffer with Tyrode's/2Ca also did not change the fluorescence plateau appreciably.

To measure cytosolic calcium concentrations, the hNT cells were loaded with the ratiometric calcium dye fura-2. Therefore, we were able to observe in the same experiment a large increase in cytosolic calcium as well as the membrane depolarization upon addition of aggregated Aβ1–42 to the cells (FIG. 1B). However, the cytosolic calcium level began at once to decrease spontaneously (desensitization), whereas the depolarization remained at a plateau. In other experiments where a longer time was allowed, the calcium level settled to a new plateau value, about twofold higher than control values (see Blanchard et al., 1997, Blanchard et al., 2000). It should be noted that the rate of decrease is very much slower than the usual rate of desensitization of, for example, AMPA channels. It is likely that the rapid influx of calcium activates the processes that normally keep cytosolic calcium levels very low, e.g. ATP-powered calcium pumps that either sequester calcium or pump it out of the cell. The end result seems to be an equilibrium between influx of calcium and pumping out/sequestering calcium.

The remaining calcium influx was completely inhibited by 20 μM CNQX, and as a result cytosolic calcium immediately decreased to control levels upon addition of CNQX. The addition of CNQX, a specific AMPA/kainate receptor blocking agent, reduced the cytosolic calcium level to close to the control value at the beginning of the experiment (FIG. 1B). For that reason we believe that AMPA/kainate channels are involved in the influx of calcium. However, the membrane depolarization plateau remained unchanged (FIG. 1A).

Figure 3:
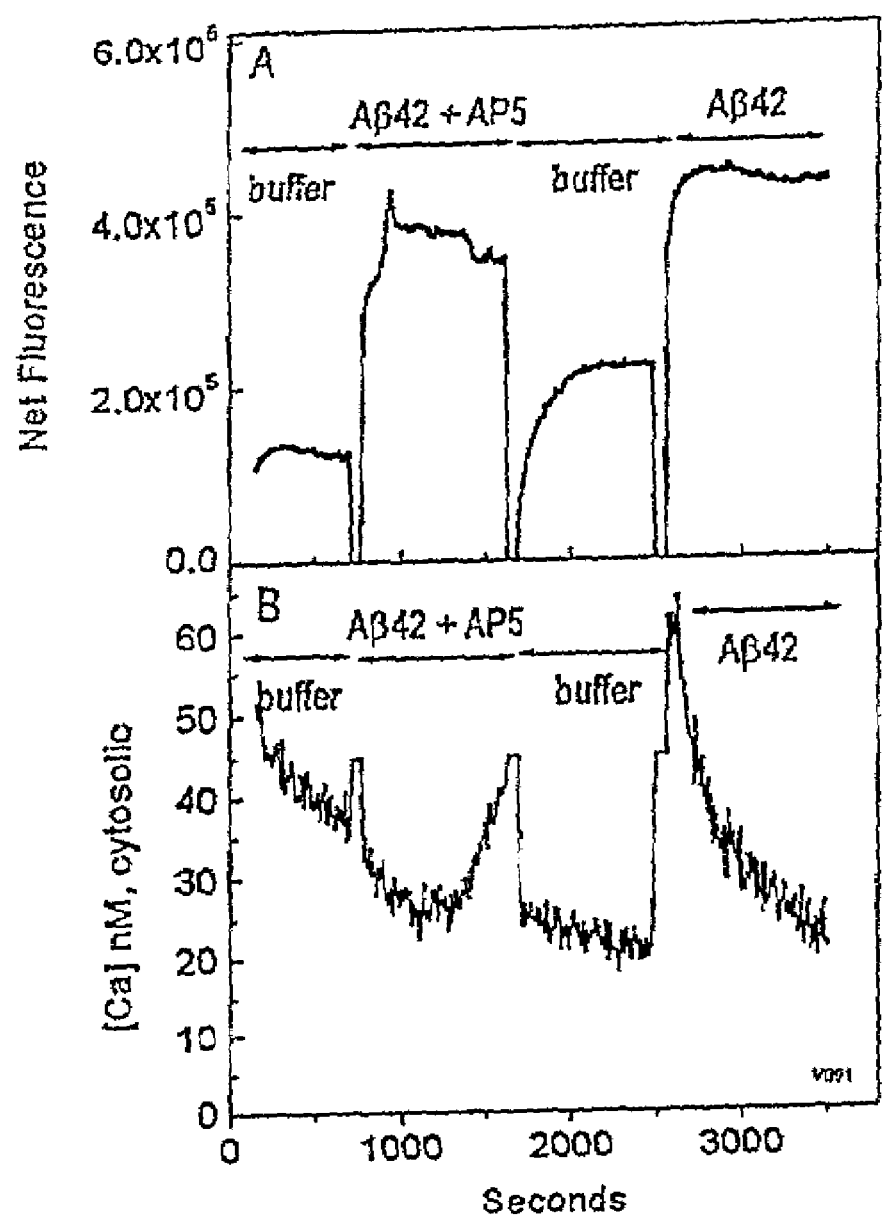
FIG. 3 shows that D-AP5, an NMDA receptor antagonist, does not block membrane depolarization by aggregated Aβ1–42 (A), but does inhibit calcium influx (B). hNT neuronal cells were exposed to aggregated 20 µM Aβ1–42 for ~1,000 sec, exchanged for Tyrode's/2Ca, which was replaced with aggregated Aβ1–42 (20 µM). Depolarization was measured with DiBAC$_4$(3), and cytosoloic calcium with fura-2.

The effect of NMDA on calcium influx also was tested. The NMDA blocker DL-AP5 was added at a concentration of 50 μM to cells with aggegated Aβ1–42 (see FIG. 3). DL-AP5 addition largely, but not completely, abolished calcium influx. As with CNQX, DL-AP5 did not interfere with the depolarization phenomenon (FIG. 3A). After washout and replacement of the external solution with just aggregated Aβ1–42, the membrane potential remained depolarized at a slightly higher level than control. The simultaneous fura-2 measurements (FIG. 3B) indicate that DL-Aβ5 inhibited much of the calcium influx, allowing only a late rise in cytosolic calcium. After washout and replacement of aggregated Aβ1–42 there was the expected sharp rise in cytosolic calcium, which then slowly declined, as usual.

Figure 4:
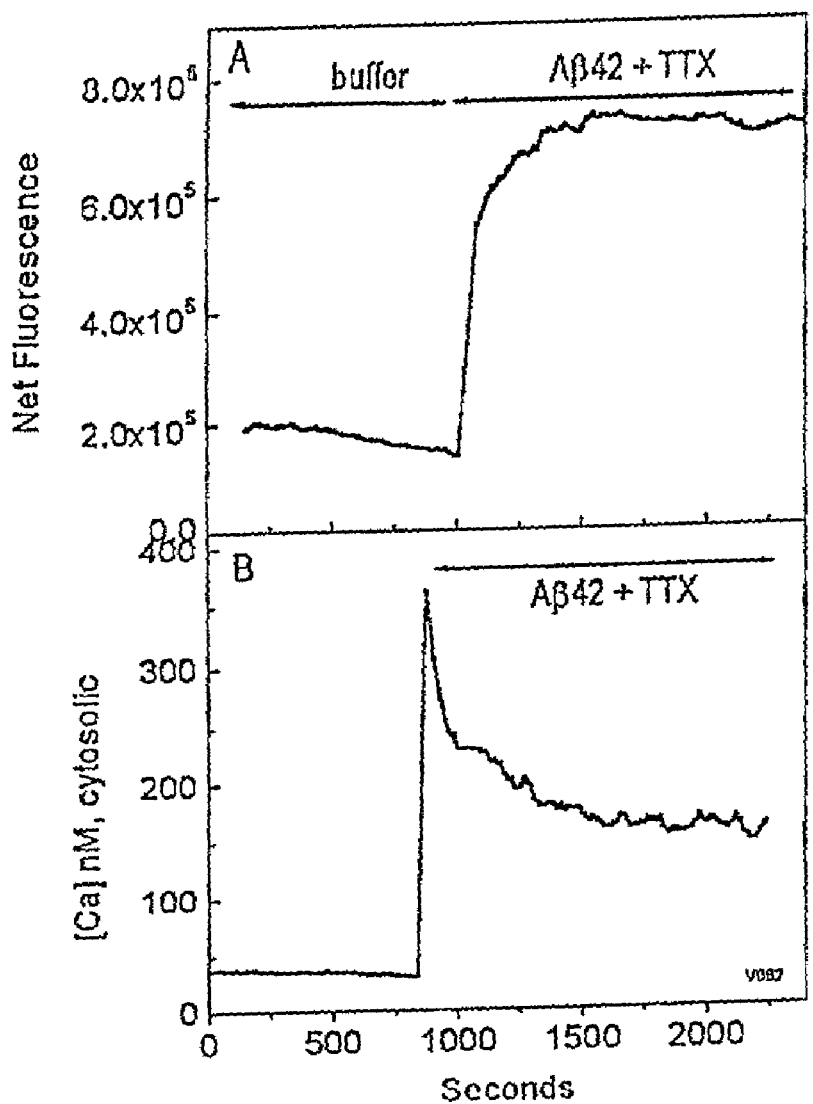
FIG. 4 is a graph depicting the effect of the presence of 1 µM tetrodotoxin (TTX), a specific sodium ion channel blocking agent, that allows both membrane depolarization (A) as measured by 100 nM DiBAC$_4$(3), and the rise in cytosolic calcium (B), as measured by fura-2, when aggregated 20 µM Aβ1–42 is added to hNT neuronal cells.

The presence of the specific sodium channel blocker tetrodotoxin (TTX) allowed both membrane depolarization and a rise in cytosolic calcium levels when pre-aggregated Aβ1–42 was added to the cells (FIG. 4). Similarly, cadmium chloride, which blocks voltage-gated calcium channels, did not prevent membrane depolarization by aggregated Aβ1–42. Thus, voltage-gated sodium channels were not involved in causing either the membrane depolarization or the influx of calcium ions.

Figure 2:
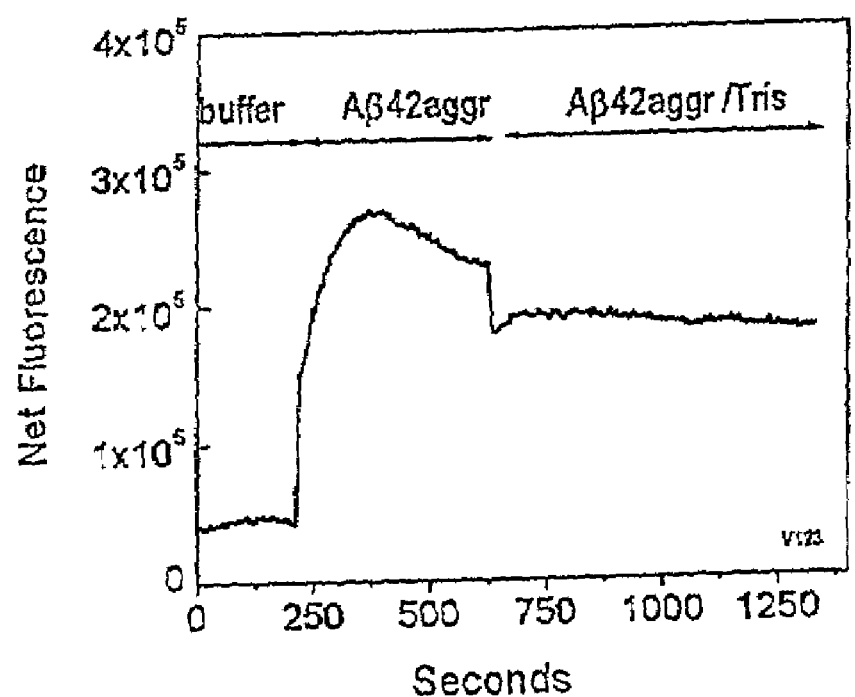

Arispe et al. have reported (*Proc. Natl. Acad. Sci. USA* 90:567–571, 1993) that the β-amyloid peptide Aβ1–40 forms a cation ionophore in artificial membranes and that this can be blocked by 10 mM TRIS$^+$. To determine whether the observed membrane depolarization is due to a similar ionophore effect, but using Aβ1–42, we exposed hNT neuronal cells to Aβ1–42 aggregates in the absence and then in the presence of 10 mM TRIS$^+$. We found a moderate decrease in membrane depolarization at 10 mM TRIS$^+$ (FIG. 2).

To test whether increased cytosolic calcium is from internal or external sources, the hNT cells were placed in Tyrode's buffer with different calcium concentrations (Table 1). Increasing external calcium from 2 mM to 10 mM made no difference to the membrane potential; however, the calcium influx became very large indeed. Decreasing external calcium to 0.4 mM decreased the membrane potential increase somewhat, but did not eliminate it (Table 1). When calcium was entirely left out of the external medium, a remarkably large increase in fluorescence was seen (FIG. 5; Table 1). We have no explanation for these last two observations. It is, of course, well known that neuronal cells need external calcium for morphological, and perhaps for membrane stability.

To test whether other external ions could take the place of Na$^+$ in the Tyrode's buffer solution and still cause depolarization, external Na$^+$ was replaced with an equal concentration of either tetraethylammonium$^+$ (TEA$^+$) or N-methyl-D-glucamine$^+$ (NMDG$^+$). These ions also allowed Aβ1–42 to cause a large membrane depolarization (FIG. 6A,B). When TEA$^+$ was used, cytosolic calcium also rose sharply as expected and then decreased (FIG. 6A'). In this particular experiment the cytosolic calcium level dipped spontaneously and quickly from the initial high value almost to control values, but then rapidly recovered to the expected high values. We have no explanation for this behavior, but have observed it on several occasions. In the TEA$^+$ experiment, depolarization was partially reversible, when the peptide was washed out (FIG. 6A). When Aβ1–42 was added to cells in Tyrode's buffer containing NMDG$^+$ (FIG. 6B) instead of Na$^+$, there was again a sharp membrane depolarization, as well as a strong increase in cytosolic calcium. However, we did not observe in this experiment a sharp initial calcium spike.

TABLE 1

Depolarization Effect of Aggregated Aβ1-42

| FIG. # | [Ca$^{2+}$] mM | ext. Cat. | Addition | % ΔF | ΔE$_M$ mV |
|---|---|---|---|---|---|
| FIG. 1 V102 | 2 | Na$^+$ | — | 15.7 | +59.7 |
| FIG. 2 V123 | 2 | Na$^+$ | — | 14.8 | +65.2 |
| — | 0.4 | Na$^+$ | — | 8.3 | +31.6 |
| — | 10 | Na$^+$ | — | 15.3 | +58.3 |
| FIG. 1 V102 | 2 | Na$^+$ | CNQX | 17.0 | +64.6 |
| FIG. 3 V091 | 2 | Na$^+$ | D-AP5 | 10.4 | +39.5 |
| FIG. 4 V082 | 2 | Na$^+$ | TTX | 17.3 | +65.7 |
| FIG. 5 b712 | 0 | Na$^+$ | — | 51.1 | * |
| FIG. 6A b677 | 2 | TEA$^+$ | — | 44.8 | * |
| FIG. 6B b756 | 2 | NMDG$^+$ | — | 44.1 | * |

* In these experiments the % ΔF is very large; the described method for deriving ΔE$_M$ may not apply.
Groups of hNT neuronal cells (5–17) were exposed to Aβ1-42 (20 μM) that had been incubated at 37° C. for 48 hours; 97 nM DiBAC$_4$(3) was present. Fluorescence was measured as described above; Ex = 490 nm, Em = 510 nm.

According to the results shown above, the membrane depolarization by aggregated Aβ1–42 is not inhibited by the simultaneous presence of the ion channel blockers CNQX or DL-AP5, separately or together. These findings distinguish the mechanism for membrane depolarization from the mechanism for calcium influx, since the latter phenomenon is inhibited by CNQX and by DL-A5. Membrane depolarization by aggregated Aβ1–42 is not dependent on external Ca$^{2+}$. Presumably it is caused by an influx of cations through an ionophore formed by the peptide (see Arispe, et al., *Proc. Natl. Acad. Sci. USA* 90: 567–571, 1993a; Arispe et al., *Proc. Natl. Acad. Sci. USA* 90: 10573–10577 1993b; and Pollard et al., *Ann. N.Y. Acad. Sci.* 695: 165–168, 1993). Moreover, we observed depolarization when external Na$^+$ was replaced by the (usually) impermeant large cations tetraethylammonium$^+$ (TEA$^+$) or N-methyl-D-glucamine$^+$ (NMDG$^+$).

Aβ1–42 was pre-incubated for 48 hrs at pH7.4 and 37° C. before applying the peptide to the neuronal cells. This was because it had been found (Blanchard et al., 1997, Blanchard et al., 2000) that such incubation was necessary to obtain a robust calcium influx. The particular peptide preparation that was used formed mostly fibrils under our aggregation conditions. The literature on the relationship between aggregation of Aβ peptides and neurotoxicity is unclear. In their early experiments, Yankner et al. (*Science* 250:279–282, 1990) did preincubate and observed cell death. Hartley et al. (1999) observed that their protofibrils, "metastable intermediates in amyloid fibril formation", can alter the electrical activity of neurons and are toxic, as was a "low molecular weight Abeta". Walsh et al. (*J. Biol. Chem.* 274:25945–52, 1999) report that their "protofibrils . . . affect the normal metabolism of cultured neurons [sic]". We also saw protofibrils in our EM experiments when the Aβ1–42 sample had not been incubated at 37° C. (Blanchard et al., 2000), but this preparation did not produce the characteristic calcium influx and was therefore deemed to be non-toxic to our cells.

In summary, it appears that aggregated Aβ1–42 acts on the type of AMPA/kainate receptors (and also NMDA receptors) present in hNT neurons that allow Ca$^{2+}$ to flow into the cell. Aggregated Aβ1–42 also acts as an ionophore admitting cations to cause membrane depolarization in neurons. Based on the results shown herein for non-Na ion influx, the ionophore structure formed by aggregated Aβ1–42 would have to be large enough to admit cations as large as TEA$^+$ and NMDG$^+$ (FIG. 6A,B), which may be the case for the so-called giant ionophores previously reported (Arispe et al., 1993a, 1993b, and Pollard et al., 1993). Several models of Aβ1–40 ionophores with the expected properties have been proposed by Durell et al. (*Biophys. J.* 67:2137–2145, 1994), but these models were proposed for Aβ1–40, not Aβ1–42. In particular, one of their models has the C-terminal portion of Aβ1–40 form α-helices which then as a group would insert into the membrane and might form an ion channel; Aβ1–42 has a similar C-terminal sequence. Their model is appealing, but does not explain the basis for the rapid interchange between "large" and "giant" ionophores.

We interpret the observed increase in DiBAC$_4$(3) fluorescence by Aβ1–42 in our hNT cells as a membrane depolarization. The magnitude of the depolarization caused by Aβ1–42 (Table 1) can be calculated from a comparison with observations when the membrane was depolarized by partially replacing Na$^+$ with K$^+$ in the bath solution and using the Nernst equilibrium. When the major external cation was Na$^+$, the observed depolarization is in the range of +13.5 to +22.6 mV. Since this is postulated to be a long-lasting, perhaps chronic state and not readily reversible, the affected neurons would be hyperexcitable and respond to certain weak stimuli that are usually ineffective. Thus we postulate this effect as a model for cognitive deficits in Alzheimer brains.

We have also observed similar depolarization effects with PC12 cells. Using undifferentiated PC12 cells in 96-well plates, the extent of membrane depolarization correlates with the concentration of aggregated Aβ(1–42,aggr). Aβ(1–42,aggr) at 10 μM was added to each well in the presence of 97 nM DiBAC$_4$(3) and fluorescence was measured in the Fluoroskan II fluorometer. The large membrane depolarization (ΔF=+117%) is not changed by the presence of either CNQX (AMPA/kainate antagonist, 20 μM) or D-AP5 (NMDA antagonist, 50 μM) or both channel antagonists together.

The aggregation of seed-free Aβ1–42, as measured with ThT, is likely to follow nucleation kinetics (Lansbury Jr., et al., Nat. Struct. Biol., 11, 1995). We found such β-sheet formation to be strongly dependent on peptide concentration. We prepared seed-free Aβ1–42, following Fezoui et al. (Amyloid Sep., 7, 2000). Unlike Fezoui et al., we did not obtain a soluble seed-free peptide preparation that was <110 kDa in size, but then we had used Aβ1–42. Our smallest soluble preparation was <10 to <30 kDa, implying oligomers of complexity 3–8. We tested the effect on membrane depolarization of different concentrations of originally seed-free Aβ1–42 after incubation at 37° C. in Tyrode's/2Ca for 48 h, using undifferentiated PC12 cells in 96-well plates. We observed a very significant increase in membrane depolarization with total Aβ1–42 or seed-free Aβ1–42, both preincubated at 37° C. for 48 h. This effect was reversible when the external solution was replaced with Tyrode's/2Ca buffer. Membrane depolarization increased with increasing peptide concentrations up to 15 μM, then levelled.

Hartley et al. (1999) recently reported acute electrophysiological changes and neurotoxicity in cultures of embryonic rat brain cells, when exposed to intermediates of Aβ1–40 aggregation. Their so-called "protofibrils", which are fibrils of intermediate length, did not cause cell death, as did fully formed fibrils. However, in patch-clamp experiments the authors were able to demonstrate that protofibrils at micromolar concentration produced a "rapid and sustained increase in electrical activity", including "increased frequencies and larger sizes of membrane depolarizations". The experiments disclosed herein were done under very different conditions, with different cells and with aggregated Aβ1–42, and permit an understanding of the molecular mechanisms involved.

The cell-type-specific distribution of neuronal damage and dysfunction determines the kind of cognitive and behavioral deficits seen in Alzheimer's Disease. It is expected that the events observed in culture reflect the in vivo situation of AD, providing a rational basis for the regional distribution of cell damage observed in AD, namely, the distribution of particular receptors. Given the drastic cellular calcium overload induced by aggregated Aβ1–42, it can be seen that cell-type specific localization of calcium overload, followed by plaques and tangles and neuronal dysfunction is likely related to the distribution of neurons with AMPA/kainate receptors of the kind that transmit Ca$^{2+}$ and with NMDA receptors. Furthermore, it is expected that increased calcium will lead to protein kinase activation, hyperphosphorylated tau and tangle formation.

Therefore, although we do not wish to be limited to any particular theory, two molecular causes are proposed for neuronal dysfunction in Alzheimer's Disease. First, pre-aggregated Aβ1–42 causes calcium influx by acting through AMPA/kainate receptors and NMDA receptors, leading to a chronic and toxic increase in cytosolic calcium levels in certain neurons. Second, aggregated Aβ1–42 causes the formation of large ionophores that admit cations and produce chronic depolarization. Both effects lead to neuronal dysfunction: the first to disturbance of calcium homeostasis and eventual cell death, the second to hyperexcitability and likely cognitive dysfunction.

Example 2

Control of Membrane Depolarization in Alzheimer's Disease

Our previous work with hNT and PC12 neuronal cells described herein and in Blanchard et al., 1997 and Blanchard et al., 2000 has shown that contacting neuronal cells with aggregated Aβ1–42 causes an immediate and pronounced membrane depolarization that interferes with normal neuronal functioning. Aβ1–42 has been shown to play an important role in Alzheimer's Disease (AD).

The experiments described herein were designed to identify, in high throughput screens, compounds that can decrease or eliminate the deleterious membrane depolarization caused when neuronal cells are contacted with pre-incubated aggregated Aβ1–42 peptide. Upon occurance of neuronal cell depolarization in the brain, affected neurons would become hyperexcitable and respond to unwanted stimuli. This might contribute to cognitive dysfunction and would occur well before cell death. Accordingly, the compounds identified herein are expected to be useful in treating the early and middle stages of Alzheimer's Disease.

We have screened a library of 1,760 compounds that are biologically active. The library consists of six 384-well plates each of which were screened in triplicate using the methods described below. The compounds can be used to block the membrane depolarization of neuronal cells caused by aggregated Aβ1–42 and thereby reverse the dysfunction such depolarization causes.

To eliminate or at least to decrease the depolarizing effect of aggregated Aβ peptides would be of great benefit to AD patients in the early and middle stages of the disease. More sensitive tests for early AD are being developed. Those testing positive for AD would be candidates for the kind of therapy being developed here: administration of one or more compounds that decrease membrane depolarization. Such therapy would also be suitable for those individuals who are judged to be vulnerable to AD for genetic reasons.

In addition, reduction or elimination of this type of dysfunction would be a necessary co-therapy to augment the expected new AD treatments—e.g. Aβ as vaccine, secretase inhibitors—which, though effective against plaque accumulation, are expected to leave considerable cognitive deficits. This residual deficit is probably due to residual membrane depolarization; this effect could be controlled or alleviated with compounds detected the high throughput screen described herein.

Method for Screening Chemical Libraries

Multiwell plates (Costar 384-well, cat. #3712; Corning Inc. Life Sciences, Acton, Mass.) were first coated with poly-D-lysine+collagen (100:1 in water) at room temperature for 2 hrs., then washed three times with sterile water using a Multidrop automatic dispenser (Thermo Labsystems Oy, Helsinki, Finland ). Undifferentiated PC12 neuronal cells were then seeded at 60,000 cells/well in 40 µl volume and incubated at 37° C. in 6%$CO_2$ for 48 hrs. The plates were washed three times with Tyr2Ca pH7.4 using a Tecan-384 power washer (Tecan Group, Ltd., Männedorf, Switzerland) with the final wash leaving 40 µl of buffer/well.

Preincubated 30 µM Aβ1–42 (in Tyr2Ca pH7.4, aggregated 37° C. for 48 hrs.) was dispensed using a Multidrop 384 plate filler with 20 µl/well to a final concentration of 10 µM/well. Each plate was set up to include Aβ1–42 and Tyr2Ca controls. The membrane fluorescent dye DiBAC4(3) was added to the Aβ1–42 and Tyr2Ca solutions to a final concentration of 100 nM.

The compounds from the 384-well library plate (thawed at room temperature and quickly centrifuged) were pin transferred using plastic polypropylene pins (384 Pin Replicator, #X5050; Genetix Limited, Hampshire, UK) into the plates with PC12 cells in rows #3–22. The pin transferred 50 nl of stock compound that was at 4 mg/ml in DMSO giving a final concentration of ~5 µg/ml/well.

Fluorescence was recorded within 5–15 min. at Ex485Em530 with a fluorescein filter set in a LJL Biosystems Analyst AD 96–384 platereader (Molecular Devices Corp., Sunnyvale, Calif.).

The data analysis involved normalization of each well by dividing the signal of each well by the mean of the Aβ1–42 control wells. Thus the maximum depolarization induced by aggregated Aβ1–42 resulted in a fluorescence value of 1.00, and no depolarization in the absence of aggregated Aβ1–42 (buffer control) resulted in a fluorescence value of ~0.6. We selected compounds that showed a reduction in membrane depolarization caused by Aβ1–42 that gave fluorescence values of <0.80. These compounds were then further screened by a concentration dependence curve of effectiveness.

The Libraries of Compounds

A random library of 1,540 compounds that are biologically active (LOPAC, purchased from Sigma-RBI (Natick, Mass.); Cat. No. SC001), consisting of six 384-well plates, each of which were screened in triplicate using the method as follows.

This library contains metabolic activators and inhibitors of cellular signaling pathways. Small molecules with defined molecular mechanisms, such as rapamycin, FK506, wortmannin, trapoxin, trichostatin and many others have been frequently used in the course of biological studies to test whether the cellular pathway or protein known to be affected by the compound is involved in a specific biological effect, such as a signal transduction cascade or a cellular phenotypes. This library contains such compounds and was assembled by selecting compounds available from Sigma Corporation with annotation describing some biological activity. These compounds were dissolved in dimethylsulfoxide (DMSO) at a concentration of 4 mg/mL and formatted in 384-well plates for screening. These are all known, published compounds; many are in use pharmaceutically for diseases other than AD. Moreover, the pharmacokinetics of most of these compounds is known, which should make it much easier for "hits" to enter clinical testing.

The screening method utilized a lawn of undifferentiated PC12 cells at the bottom of each well in a 384 well plate. The cells were treated with a suspension of pre-incubated Aβ1–42 peptide at 10 µM. Changes in membrane potential were detected with DiBAC4(3), a slow voltage-sensitive fluorescent dye. This treatment produced a long-lasting, ~100% increase in gross fluorescence. The controls were PC12 cells not treated with Aβ1–42 (i.e., buffer-only controls). Multiple wells were used for control and for Aβ itself.

To screen for compounds that reduce membrane depolarization induced by Aβ1–42, single compounds from a chemical library were added to single wells, at a fixed concentration of 4 µg/mL or ~10 µM, depending on the molecular weight of the compound. A "hit" was a compound that reduces the gross fluorescence as close to the fluorescence seen without Aβ1–42 as possible, i.e., a compound that restores normal membrane depolarization status.

Each 384-well plate contained 32 wells (2 columns of 16 wells each) with Aβ1–42 only (+Aβ control) and 16 control wells (1 column) with the buffer Tyrode's/2Ca (buffer control (−Aβ control)). In addition there were 320 wells per plate containing 1 test compound each.

The test was repeated several times and the mean for each test compound was calculated. The gross fluorescence for each test well was divided by the mean fluorescence of the +Aβ wells. Thus, maximum depolarization yielded a fluorescence =1.00, while the −Aβ control yielded a fluorescence =~0.6. The mean values for each test compound are sorted by increasing value.

We chose to concentrate only on those compounds that gave values <0.8. These compounds, regarded as preferred hits, were then characterized individually by constructing a concentration curve of effectiveness. We have so far examined 10 of the most preferred hits out of the 37 preferred hits shown in Table 2 and additional hits identified by additional screening. The surprisingly high number of hits is no doubt due to the fact that the libraries are not random compounds, but are all pharmacologically active compounds.

The initial search of the libraries used compounds dissolved in the "universal" solvent DMSO. Since DMSO itself lowers membrane potential, the concentration curves are done in purely aqueous solution, whenever possible. Otherwise, the appropriate solvent controls are done. We have so far concentrated on those compounds that are water-soluble.

TABLE 2

Results of Preliminary Screen for Compounds that Reduce the Membrane Depolarization Caused by Aggregated Aβ1-42

| RFU | p | Code | Name | Sigma # | Function |
|---|---|---|---|---|---|
| 0.49 | <0.10 | LO002C10 | 4,5-Dianilinophthalimide | D210 | Tyrosine kinase inhibitor, selective for EGF receptor |
| 0.59 | 0.01 | AS002F11 | Nafoxidine HCl | N6632 | Anti-estrogen |
| 0.62 | <0.20 | AS001N12 | Theobromine | T4500 | Phosphodiesterase inhibitor |
| 0.65 | <0.20 | LO002D20 | Tamoxifen citrate | T126 | PKC inhibitor; induces apoptosis |
| 0.71 | <0.10 | AS003N18 | Actinonin | A6671 | Leucine aminopeptidase inhibitor |
| 0.72 | <0.20 | AS002D11 | 6-Nitroso-1,2-benzopyrone | N8403 | ADP-ribosyl-transferase inhibitor (Zn sites) |
| 0.73 | <0.10 | LO001F21 | (±)-Vanillylmandelic acid | V103 | Catecholamine Metabolite |
| 0.74 | >0.20 | LO002C21 | D-Serine | S135 | Active at strychnine-insensitive glycine binding site, NMDA receptor as well as the inhibitory post-synaptic glycine receptor |
| 0.75 | <0.20 | LO002F20 | Tamoxifen, 3-hydroxy, citrate | T171 | Anti-estrogen ? |
| 0.75 | <0.20 | AS001D03 | Proglumide Free acid | P4160 | Selective cholecystokinin receptor antagonist |
| 0.75 | <0.10 | AS002D03 | Leupeptin Hydrochloride | L0649 | Protease inhibitor. |
| 0.76 | <0.05 | LO001N18 | Pergolide methanesulfonate | P168 | Dopaminergic agonist; antiparkinsonian |
| 0.76 | <0.01 | AS004E11 | D-(−)-2-Amino-4-Phosphono-butyric acid | A7804 | First generation NMDA antagonist. |
| 0.76 | <0.05 | LO002E11 | 1,10-Diaminodecane | D140 | NMDA/Polyamine site |
| 0.76 | 0.2 | AS003C10 | Flutamide | F9397 | Anti-Na+/hKv |
| 0.76 | <0.20 | AS003C22 | Propafenone Hydrochloride | P4670 | K+ ion signaling: blocks tonic and phasic Na+ channels and hKv 1.5 and ATP-sensitive K+ channels; class 1C antiarrhythmic agent that is also an antagonist at beta adrenergic receptors |
| 0.77 | <0.20 | AS002D05 | Omeprazole | O104 | H+/K+ ATPase inhibitor |
| 0.77 | 0.2 | AS003C18 | Nadolol | N1892 | beta-Adrenergic blocker |
| 0.78 | <0.05 | AS003A15 | Chlorotrianisene | C7128 | Nuclear hormone receptor; estrogenic agent |
| 0.78 | <0.20 | AS003C20 | Oxymetazoline Hydrochloride | O2378 | Partial α2a-adrenergic agonist, agonist at 5-HT1A, 5-HT1B and 5-HT1D receptors and a mixed agonist-antagonist at 5-HT1C receptors |
| 0.78 | 0.20 | LO001F20 | Rauwolscine hydrochloride | R104 | α2-adrenergic receptor antagonist; 5-HT1A serotonergic receptor agonist |
| 0.78 | <0.10 | LO001N20 | (±)-6-Chloro-PB hydrobromide (SKF81297) | S143 | Full D1 dopamine receptor agonist |
| 0.78 | <0.005 | LO001N22 | R(+)-Terguride | T165 | Dopamine receptor partial agonist. |
| 0.78 | 0.2 | AS003K09 | Thioridazine Hydrochloride | T9025 | D2 dopaminergic antagonist; phenothazine antipsychotic with reduced extrapyramidal side effects; Ca2+ channel blocker. |
| 0.78 | <0.20 | AS001D07 | Mycophenolic acid | M5255 | Immunosuppressive agent. Suppresses cytokine-induced nitric oxide production. Inhibitor of inosine 5'-monophosphate dehydrogenase |
| 0.79 | <0.005 | AS004E22 | Cysteamine S-phosphate Sodium Salt | C8397 | ? |
| 0.79 | <0.05 | AS001G18 | 5-amino-7-br-4-oxo-3-p-tolyl-thieno 3,4-dâpyridazine-1-carboxylic acid et ester | S297755 | ? |
| 0.79 | >0.20 | AS002D17 | D-Mannitol | M9546 | Diuretic |
| 0.79 | >>0.20 | AS002B11 | N-Oleoylethanolamine | O0382 | Ceramidase inhibitor |
| 0.79 | <0.20 | AS002M08 | α-Methyl-DL-aspartic acid | M6001 | NMDA agonist |
| 0.80 | >0.20 | AS003C08 | Famotidine | F6889 | Histamine H2 receptor antagonist |
| 0.80 | >0.20 | AS003O21 | Aconitine | A8001 | Neurotoxin; activates tetrodotoxin-sensitive Na+ channels |
| 0.80 | <0.20 | AS002D07 | β-N-oxalylamino-L-alanine | O5382 | Glutamate agonist; excitotoxic amino acid |
| 0.80 | <0.05 | AS004D19 | Aprotinin | A6279 | Serine protease inhibitor that inhibits trypsin, chymotrypsin, kallikrein and plasmin |

RFU: relative fluoroscent units;
a value of 1.00 = full depolarization (+Aβ control);
a value of ~0.6 = no depolarization (= buffer control (−Aβ))
a value of <0.6 = hyperpolarization
p: gives the statistical significance of the RFU
code: code number for the location of a particular compound in the libraries.
Name: chemical name of the compound
Sigma #: Sigma Chemical Co. catalog number.
Function: the function of thee compound as described in the Sigma catalog RFU: relative fluoroscent units;
 a value of 1.00full depolarization (+Aβcontrol);
 a value of ~0.6=no depolarization (=buffer control (−Aβ))
 a value of ≦0.6=hyperpolarization
p: gives the statistical significance of the RFU
code: code number for the location of a particular compound in the libraries.
Name: chemical name of the compound
Sigma #: Sigma Chemical Co. catalog number
Function: the function of thee compound as described in the Sigma catalog Further Screens to Identify Preferred Compounds FIG. 7 shows the results of the screen after sorting the compounds by relative fluorescence values (RFUs). We selected 10 compounds for further study, listed alphabetically in Table 3, together with their known biological function.

TABLE 3

List of "best hit" compounds:

| Name | Function |
| --- | --- |
| Clomiphene | Inhibits voltage-regulated anion channels, anti-estrogen |
| 4,5-Dianilino-phthalimide (DAPH1) | Protein tyrosine kinase inhibitor, with selectivity for the epidermal growth factor (EGF) receptor. |
| Dopamine | Dopamine receptor agonist |
| Nafoxidine | Anti-estrogen; inhibits certain Cl⁻ channels |
| Rauwolscine (= α-yohimbine) | alpha2-Adrenergic receptor antagonist; 5-HT1A serotonergic receptor agonist. |
| SKF81297 (6-Cl-PB HBr) | Full D1 dopamine receptor agonist |
| Tyrphostin 47 | EGF receptor tyrosine kinase inhibitor. $IC_{50} = 2.4\ \mu M$ |
| Tyrphostin AG 879 | Tyrosine kinase inhibitor; specific for nerve growth factor receptor, TrkA. Also inhibits trk protooncogene and HER-2. |
| Vanillylmandelic Acid | Dopamine receptor agonist |
| Substance P | NK1 agonist |

The list includes dopamine itself, although this did not show in the screen, because two dopamine agonists, rauwolscine and SKF81297, were identified in the high-throughput screen. The neuropeptide Substance P, an NK1 agonist, was also included, because Yankner et al. (1990) described its ability to eliminate the neurotoxicity of Aβ25–35.

The characterization of these hit compounds was by multiple assays at different concentrations, using 96-well plates and quadruple assays. Grouping the hit compounds by function gives the list shown in Table 4.

TABLE 4

Effectiveness of "Best Hit" Compounds

| Name | [Aβ] | Decrease of ΔF at 10 μM compound (%) | Hyper-polarization ΔF % |
| --- | --- | --- | --- |
| Tyr-Kinase Inhib. (EGF) | | | |
| 4,5-Dianilinophthalimide (DAPH1)* | 10 μM | −79 | −26 |
|  |  | −74 |  |
|  | 5 μM | −75 |  |
|  | 2 μM | −96 |  |
| Tyrphostin 47 | 10 μM | −13 |  |
|  | 2 μM | −43 |  |
| Tyr-Kinase Inhib. (TrkA) | | | |
| Tyrphostin AG 879 | 10 μM | −73 |  |
|  | 5 μM | −68 |  |
|  | 2 μM | −95 |  |
| Cl⁻ Channel Antagonists | | | |
| Nafoxidine *** | 10 μM | −49 | −41 |
|  | 5 μM | −100 |  |
|  |  | −74 |  |
|  | 2 μM | −124 |  |
| Clomiphene # | 10 μM | −19 | −11 |
|  | 5 μM | −16 |  |
|  | 2 μM | −38 |  |
| Dopamine Agonists | | | |
| SKF81297 (6-Cl-PB) | 10 μM | −30 |  |
|  | 5 μM | −14 | −1 |
|  | 10 μM | −29 |  |
| Vanillyl-Mandelic Acid | 10 μM | −26 |  |
|  |  | −17 |  |
|  | 5 μM | −21 | −13 |
|  | 10 μM | −17 |  |
| Dopamine | 10 μM | −14 |  |
|  |  | −48 |  |
|  | 2 μM | −55 |  |
|  | 10 μM |  |  |
| alpha2-Adrenergic receptor antagonist; 5-HT1A serotonergic receptor agonist. | | | |
| Rauwolscine (α-yohimbine) | 10 μM | −79 | −27 |
|  | 10 μM | −14 |  |
|  | 5 μM | −12 |  |
|  | 2 μM | −37 |  |
| TK1 antagonist | | | |
| Substance P ** | 10 μM | −25 | −25 |

*DAPH1 at 2 μM and Aβ1-42 at 10 μM, ΔF = −19%.
** not in the screen
*** NAF at 2 μM and Aβ1-42 at 10 μM, ΔF = −34% (V352)
CLO at 2 μM and Aβ1-42 at 10 μM, ΔF = 14%

The most effective elimination of depolarization was achieved with two tyrosine kinase inhibitors, DAPH1 (4,5-dianilinophthalimide, EGF-receptor specific) and Tyrphostin AG879 (TrkA specific), and also nafoxidine (anti-estrogen receptor, chloride channel antagonist). These were active in low micromolar concentration (FIGS. 8, 9). Tyrphostin 47 (EGF receptor tyrosine kinase inhibitor) is less effective. Five other tyrosine kinase inhibitors were inactive (FIG. 8). Not all compounds that seemed to be promising "hits" after the screen were confirmed after characterization in detail.

The following tyrosine kinase inhibitors were inactive in our characterization assay. They had not been detected in the screen, but were tested because they might be functionally related to those tyrosine kinase inhibitors that did appear in the screen:

| Genistein | Inhibitor of tyrosine protein kinase; competitive inhibitor of ATP in other protein kinase reactions (Akiyama et al., 1987). |
| --- | --- |
| Herbimycin A | Tyrosine kinase inhibitor; cell permeable; inhibits platelet derived growth factor induced phospholipase D activation (O'Dell et al., 1991). |
| Lavendustin A | Cell permeable inhibitor of tyrosine kinase with little effect on protein kinase A or C; inhibits NMDA-stimulated cGMP production (Huang et al., 1992). |
| Tyrphostin AG 1295 | Selective inhibitor of tyrosine kinase in platelet-derived growth factor (PDGF) receptor (Hakansson and Allen, 1995). |
| Tyrphostin AG 1478 | Selective inhibitor of tyrosine kinase in epidermal growth factor (EGF) receptor (Igarashin and Komiya, 1991). |

The dopamine agonists SKF81297, vanillylmandelic acid and dopamine itself were also effective in reducing depolarization, but less so. We note that the activated receptors are not ion channels themselves, but act to activate via G-proteins. The serotonergic receptor agonist rauwolscine (α-yohimbine) is also effective.

Some of these compounds when added to PC12 cells without Aβ1–42 produce a hyperpolarization (Table 4, FIGS. 8–10).

Mechanism of Decreasing Membrane Depolarization

We assume that Aβ1–42$_{aggregated}$ interacts with a receptor molecule (referred to as "receptor X") on the cell surface. One possible mechanism for depolarization is that an ion channel opens that allows Na$^+$ to flow into the cell thereby depolarizing the membrane upon interaction of Aβ1–42$_{aggregated}$ with receptor X. In this mechanism, the ion channel opens via an intermediate mechanism.

It is also possible that receptor X is itself an ion channel admitting Na$^+$. We have investigated whether NMDA and/or AMPA/kainate receptor channels play a role in the depolarization mechanism. As shown above in Example 1, membrane depolarization was not changed by the presence of either CNQX (AMPA/kainate antagonist, 20 μM) or D-AP5 (NMDA antagonist, 50 μM) or both channel antagonists together. Thus we conclude that Aβ(1–42,aggr)-induced depolarization is independent of calcium influx.

We also investigated the possible role of metabotropic glutamate receptors (mGlu receptors) in the depolarization phenomenon. mGluR antagonists and agonists were obtained (Tocris Cookson Ltd., Avonmouth, United Kingdom). After pre-incubating PC 12 cells for 30 min with various mGlu receptor antagonists, we observed a significant decrease in depolarization when we used three mGluR$_1$ antagonists, AIDA, LY367385 (denoted as LY36 in the figure), and (S)-MCPG, which are Group I mGluR antagonists with a specificity for mGluR$_1$ over mGluR$_5$ (FIG. 11). (S)-MCPG is particularly effective and at 1 mM causes a 73% decrease in depolarization. The small decrease in membrane potential observed when cells were treated with the antagonists alone may be due to elimination of a small membrane depolarization caused by residual glutamate left over from the growth medium.

Other mGlu receptor antagonists were tested in the presence of aggregated 10 μM Aβ(1–42,aggr). Two other Group I mGluR antagonists, MPEP-HCl at 0.12–5 μM and SIB1757 at 10 μM, had very little if any effect on depolarization when in combination with Aβ(1–42, aggr.). Both MPEP-HCl and SIB1757 have specificity for mGluR$_5$ over mGluR$_1$. This suggests that mGluR$_1$ and not mGluR$_5$ is the preferred site for AP-induced depolarization. The Group II/III mGluR antagonists: LY341495 (0.06–100 μM), MCCG (1 mM), EGLU (1 mM), and MPPG (1 mM) were also tested. These compounds had very little, if any effect on membrane potential, either in combination with Aβ (1–42, aggr) or by themselves.

We also found that the Aβ(1–42,aggr)-induced membrane depolarization is sensitive to pre-incubation of the PC12 cells overnight at 37° C. with pertussis or cholera toxin (Sigma). This indicates the involvement of members of the Gα0, Gαs, Gαi families of G-proteins in the depolarization phenomenon. The activation of linked G-proteins might include long-term inhibition of particular K-channels.

We found that mGluR agonists of Group I by themselves cause considerable membrane depolarization similar to Aβ(1–42 aggr.) in PC12 cells. The Group I agonists (R,S) 3,5-DHPG, (S)3,5-DHPG, (S)3H-PG, and MAP4, which are selective for mGluR$_1$ and mGluR$_5$, gave an average increase in gross fluorescence (ΔF) of 63%. While this is very significant, it is less than the depolarization caused by 10 μM Aβ(1–42, aggr.). By comparison agonists of Group II and Group III showed very little effect, but it is not clear that our strain of PC12 cells even contain these receptors.

We reported earlier that Aβ(1–42, aggr.) also causes Ca$^{2+}$ influx. The simplest explanation is that the influx is a consequence of mGluR activation. Alternatively, there might be coincidental interaction between Aβ(1–42 aggr.) and Ca-permeant AMPA/NMDA receptors, activating them. Therefore depolarization and calcium influx are either two downstream effects of mGluR$_1$ activation or they are two independent pathways.

Additionally, we know that there is a conformational change during pre-incubation of the peptide, but a chemical modification cannot at this time be ruled out. The extracellular glutamate binding bibbed domain of the mGluRs has sequence homology with bacterial periplasmic amino acid binding proteins (Kovalenko, et al., Cancer Res. 54, 1994; Osherov, et al., Eur. J. Biochem. 225, 1994). Aggregation of Aβ1–42 might create a molecule with two "active sites" that promote receptor activation dimerization.

The foregoing examples identified compounds that reduce or eliminate the depolarization effect and at least some of the intermediaries by which the activated mGlu receptors control the membrane potential. These compounds interfere with steps in the cascade postulated to produce depolarization, for instance, certain tyrosine kinase inhibitors and others that compensate for the depolarization by causing hyperpolarization of the membrane. We deduce that these kinases and channels are normally activated to some extent by glutamate via mGluR$_1$ receptors contributing to the control of normal membrane potential of the cell. Presumably their activation is greatly increased by the aggregated Aβ1–42 peptide. Compounds that cause hyperpolarization of the membrane include dopaminergic and serotonergic agonists which are normally involved in signal transmission rather than maintenance.

Therefore, there are at least three likely mechanisms for eliminating/decreasing the membrane depolarization:

1. We can find an antagonist to the interaction of Aβ1–42$_{aggregated}$ and displace the peptide. Substance P may fit in this category.

2. If an intermediate messenger is involved, then compounds that inhibit the intermediate step may also inhibit depolarization. Some of the hits described herein probably fall into this category.

3. Compounds that compensate for the increased depolarization by causing hyperpolarization would decrease depolarization. The hits described herein are being tested for such a property. Among the hits described herein, it is possible that rauwolscine, vanillylmandelic acid and SKF81297 fall into this category.

Other potential mechanisms for decreasing depolarization include non-competitive inhibition of Aβ1–42$_{aggregated}$ binding to mGlu receptors.

REFERENCES

1. Sanderson et al., (1997) *Brain Res.* 744:7–14.
2. Blanchard et al., (1997) *Brain Res.* 776:40–50.
3. Blanchard, B. J., Hiniker, A. E., Lu, C. C., Margolin, Y., Yu, A. S. & Ingram, V. M., (2000) *J. Alzheimer's Disease* 2(2):137–149.
4. Hartley, D. M., Walsh, D. M., Ye, C. P., Diehl, T., Vasquez, S., Vassilev, P. M., Teplow, D. P. & Selkoe, D. J. (1999) *J. Neuroscience* 19:8876–8884.
5. Hartinger, J., & Jahn, R. (1993) *J. Biol. Chem.* 268: 23122–23127.
6. Cooper, C. E., Bruce, D., & Nicholls, P. (1990) *Biochemistry.* 29:3859–3865.

7. Langheinrich, U. & Daut, J. (1997) *J. Physiol.* 502: 397–408.
8. Bräuner, T., Hülser, D. F., & Strassr, R. J. (1984) *Biochimica et Biophysica Acta* 771:2208–216.
9. Arispe, N., Rojas, E., & Pollard, H. B. (1993)) *Proc. Natl. Acad. Sci. USA* 90:567–571.
10. Arispe, N., Pollard, H. B., & Rojas, E. (1993) *Proc. Natl. Acad. Sci. USA* 90:10573–10577.
11. Pollard, H. B., Rojas, E., & Arispe, N. (1993) *Ann. N.Y Acad. Sci.* 695:165–168.
12. Kawahara, M., Arispe, N., Kuroda, Y., & Rojas, E. (1997) *Biophys. J.* 73:67–75.
13. Yankner, B. A., Duffy, L. K. & Kirschner, D. A. (1990). *Science.* 250:279–282.
14. Walsh, D. M., Hartley, D. M., Kusumoto, Y., Fezoui, Y., Condron, M. M., Lomakin, A., Benedek, G. B., Selkoe, D. J. & Teplow, D. B. (1999) *J. Biol. Chem.* 274:25945–52.
15. Durell, S. R., Guy, H. R., Arispe, N., Rojas, E., & Pollard H. B. (1994) *Biophys. J.* 67:2137–2145.
16. Akiyama, T., et al., *J. Biol. Chem.*, 262, 5592–5595 (1987).
17. O'Dell, T. J., et al., *Nature*, 353, 558–560 (1991).
18. Huang J., et al., *J. Biol. Chem.*, 267, 15511–15515 (1992).
19. Hakansson, G., and Allen, J. F., *FEBS Lett.*, 372, 238–242 (1995).
20. Igarashi, M., and Komiya, Y., *J. Neurosci. Res.*, 30, 266–274 (1991)
21. P. T. Lansbury Jr., Costa, J. M. Griffiths, E. J. Simon, M. Auger, K. J. Halverson, D. A. Kocisko, Z. S. Hendsch, T. T. Ashburn, R. G. Spence, et al., *Nat. Struct. Biol.* 11, 990–998 (1995).
22. Y. Fezoui, D. M. Hartley, J. D. Harper, R. Khurana, D. M. Walsh, M. M. Condron, D. J. Selkoe, P. T. Lansbury, Jr., A. L. Fink, D. B. Teplow, *Amyloid* Sep. 7 (3), 166–178 (2000).
23. M. Kovalenko, A. Gazit, A. Bhomer, C. Rorsman, L. Ronnstrand, C. H. Heldin, J. Waltenberger, F. D. Bohmer, A. Levitzki, *Cancer Res.* 54, 6106–6114 (1994).
24. N. Osherov, A. Levitzki, *Eur. J. Biochem.* 225, 1047–1053 (1994).

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

---

We claim:

1. A composition comprising DAPH1 (4,5-dianilinophthalimide), and a secretase inhibitor.

2. A method for treating Alzheimer's disease, comprising administering to the subject an effective amount of the composition of claim 1.

* * * * *